(12) United States Patent
Sano et al.

(10) Patent No.: US 12,175,720 B2
(45) Date of Patent: Dec. 24, 2024

(54) FEATURE QUANTITY EXTRACTING DEVICE, FEATURE QUANTITY EXTRACTING METHOD, IDENTIFICATION DEVICE, IDENTIFICATION METHOD, AND PROGRAM

(71) Applicants: SHINSHU UNIVERSITY, Matsumoto (JP); CASIO COMPUTER CO., LTD., Tokyo (JP)

(72) Inventors: Tasuku Sano, Azumino (JP); Ryuhei Okuyama, Matsumoto (JP); Akane Minagawa, Matsumoto (JP); Yoshihiro Teshima, Higashimurayama (JP); Akira Hamada, Sagamihara (JP)

(73) Assignees: SHINSHU UNIVERSITY, Nagano (JP); CASIO COMPUTER CO., LTD., Tokyo (JP)

( * ) Notice: Subject to any disclaimer, the term of this patent is extended or adjusted under 35 U.S.C. 154(b) by 393 days.

(21) Appl. No.: 17/620,672

(22) PCT Filed: Mar. 25, 2020

(86) PCT No.: PCT/JP2020/013225
§ 371 (c)(1),
(2) Date: Dec. 17, 2021

(87) PCT Pub. No.: WO2020/255517
PCT Pub. Date: Dec. 24, 2020

(65) Prior Publication Data
US 2022/0245919 A1    Aug. 4, 2022

(30) Foreign Application Priority Data

Jun. 19, 2019  (JP) .................................. 2019-113990
Mar. 13, 2020  (JP) .................................. 2020-043778

(51) Int. Cl.
*G06V 10/20* (2022.01)
*A61B 5/00* (2006.01)
(Continued)

(52) U.S. Cl.
CPC ............ *G06V 10/255* (2022.01); *A61B 5/441* (2013.01); *G06T 7/0012* (2013.01); *G06V 10/25* (2022.01); *G06T 2207/30088* (2013.01)

(58) Field of Classification Search
None
See application file for complete search history.

(56) References Cited

U.S. PATENT DOCUMENTS

| 9,589,374 B1 | 3/2017 | Gao et al. |
| 2013/0243288 A1* | 9/2013 | Goto ........................ G06T 5/92 |
| | | 382/128 |

FOREIGN PATENT DOCUMENTS

| CN | 103228214 A | 7/2013 |
| JP | 2011123045 A | 6/2011 |
| JP | 2016115248 A | 6/2016 |

OTHER PUBLICATIONS

Japanese Office Action (and an English language translation thereof) dated Jan. 23, 2024, issued in counterpart Japanese Application No. 2022-133096.

(Continued)

*Primary Examiner* — Leon Flores
(74) *Attorney, Agent, or Firm* — Holtz, Holtz & Volek PC

(57) ABSTRACT

An identification device includes an acquirer for acquiring a captured image obtained by imaging a predetermined target, a specifier for specifying a linear region extending in a plurality of mutually different directions, from a region of the captured image acquired by the acquirer, the region including the predetermined target, and an extractor for (Continued)

extracting a feature quantity based on the pixel value, from the linear region specified by the specifier.

18 Claims, 11 Drawing Sheets

(51) Int. Cl.
*G06T 7/00* (2017.01)
*G06V 10/25* (2022.01)

(56) References Cited

OTHER PUBLICATIONS

International Search Report (ISR) (and English language translation thereof) dated Jun. 30, 2020 issued in International Application No. PCT/JP2020/013225.
Written Opinion dated Jun. 30, 2020, issued in International Application No. PCT/JP2020/013225.
Codella, et al., "Deep learning ensembles for melanoma recognition in dermoscopy images", IBM Journal of Research and Development, vol. 61, No. 4/5, 2017.
Lu, et al., "Color image retrieval technique based on color features and image bitmap", Information Processing and Management [online], 2007, vol. 43, pp. 461-472, [retrieved on Jun. 17, 2020], Retrieved from the Internet <URL: http://msn.iecs.fcu.edu.tw;/ccc/profile/publish/ij_paper2/ IJ-427.pdf>.
Chinese Office Action (and an English language translation thereof) dated Oct. 12, 2024, issued in counterpart Chinese Application No. 202080044494.7.

\* cited by examiner

FEATURE QUANTITY EXTRACTING DEVICE, FEATURE QUANTITY EXTRACTING METHOD, IDENTIFICATION DEVICE, IDENTIFICATION METHOD, AND PROGRAM

TECHNICAL FIELD

The present disclosure relates to a feature quantity extracting device, a feature quantity extracting method, an identification device, an identification method, and a program.

BACKGROUND ART

Conventionally, a camera is used to capture an image of a diagnostic target being part of human skin to be diagnosed, such as a mole, and the captured image is used to support a diagnosis of the diagnostic target. For example, in a technique disclosed in NPL 1, for such diagnostic support, an overall captured image including many parts of skin other than the diagnostic target and a cropped image in which the diagnostic target is cropped from the overall captured image are acquired, a plurality of feature quantities such as a color histogram are extracted from each of the acquired overall captured image and the cropped image, each of the plurality of extracted feature quantities is input into its corresponding identifier of a plurality of identifiers, and by averaging the plurality of acquired outputs of the identifiers, a disease risk score representing whether the diagnostic target is diseased or not is calculated.

CITATION LIST

Non Patent Literature

Non Patent Literature 1 (NPL 1): N. C. F. Codella, Q. B. Nguyen, S. Pankanti, D. Gutman, B. Helba, A. Halpern, J. R. Smith, "Deep learning ensembles for melanoma recognition in dermoscopy images", IBM Journal of Research and Development, vol. 61, no. 4/5, 2017

SUMMARY OF INVENTION

Technical Problem

In the technique disclosed in NPL 1, a processing load for the extraction becomes excessive because the feature quantities are extracted from each of the overall captured image and the cropped image, in other words, two-dimensional images. In order to reduce such a load of processing, it is conceivable to specify some regions of a diagnostic target in the captured image, and to extract a feature quantity from the specified regions, however, such processing may result in an inability to appropriately extract a feature quantity for the diagnostic target, and subsequently, an inability to appropriately identify a disease using the disease risk score. The above-mentioned problem applies not only to an extraction of a feature quantity of a diagnostic target on human skin, but also to an extraction of a feature quantity of an arbitrary target including a plurality of regions whose at least one of colors and luminance is mutually different, such as a feature quantity extraction of a diagnostic target on a human uterine cervix, for example.

The present disclosure has been made to solve the above problem, and an objective is to provide a feature quantity extracting device, a feature quantity extracting method, an identification device, an identification method, and a program that can appropriately extract a feature quantity while suppressing the extraction load thereof.

Solution to Problem

In order to achieve the above objective, a feature quantity extracting device of the present disclosure includes:
  acquiring means for acquiring a captured image obtained by imaging a predetermined target;
  specifying means for specifying a linear region extending in a plurality of mutually different directions, from a region of the captured image acquired by the acquiring means, the region including the predetermined target; and
  extracting means for extracting a feature quantity based on a pixel value, from the linear region specified by the specifying means.

Advantageous Effects of Invention

According to the present disclosure, a feature quantity can be appropriately extracted while suppressing the extraction load thereof.

DESCRIPTION OF EMBODIMENTS

Figure 1:
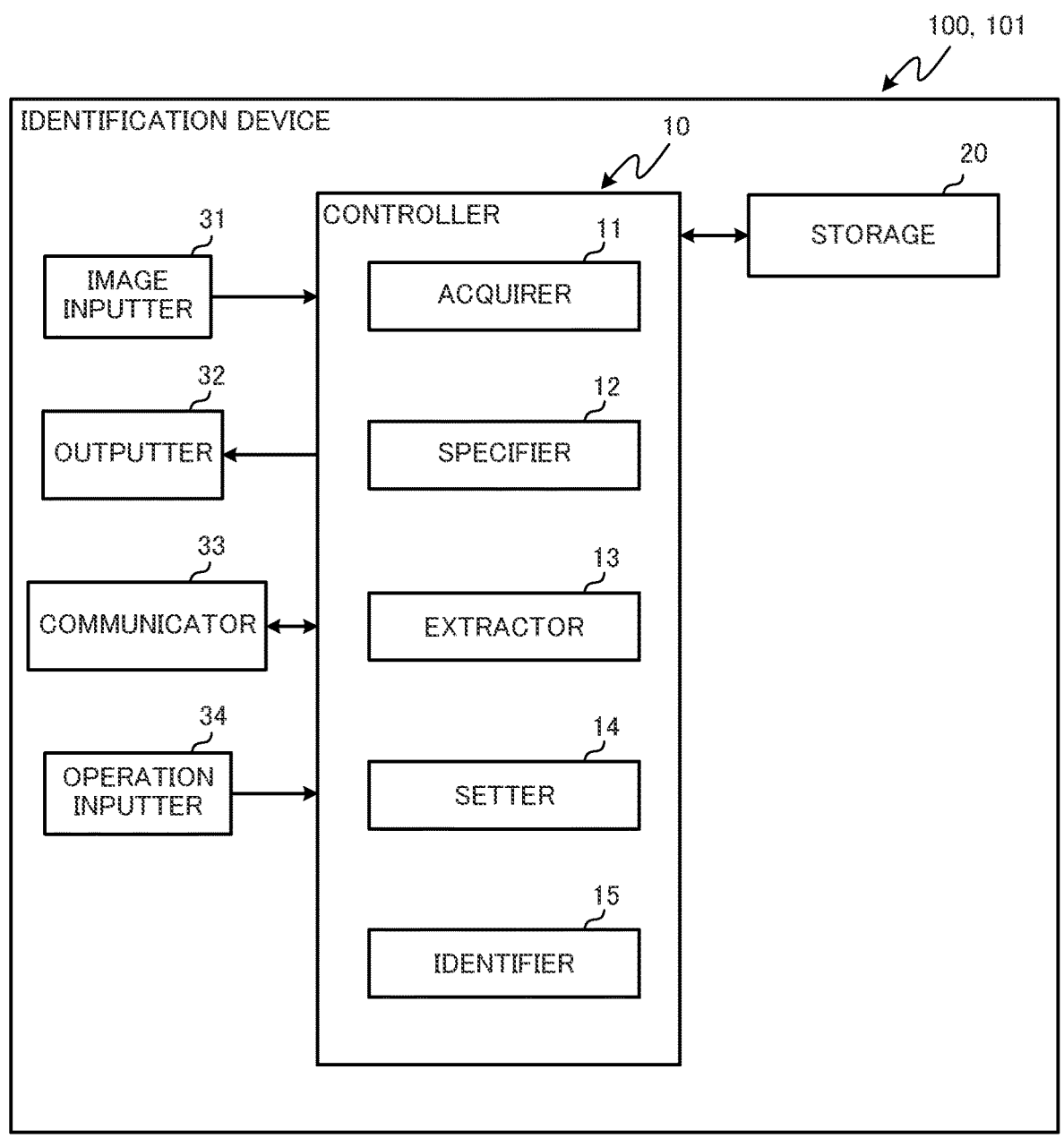
FIG. 1 is a diagram illustrating a functional configuration of an identification device according to Embodiment 1.

Hereinafter, an identification device and the like according to the embodiments of the present disclosure will be described with reference to the drawings. Same reference signs are given to same or equivalent elements.

Embodiment 1

An identification device 100 according to Embodiment 1 of the present disclosure is a device for identifying a predetermined target based on a captured image obtained by imaging the predetermined target. For example, the identification device 100 determines whether a diagnostic target in an image is benign or malignant based on a captured image of human skin including a diagnostic target (a tumor, a mole, a skin spot, a blotch, a blood vessel, atopic eczema and drug eruption, a diseased part on skin such as eruption caused by collagen disease, an area of suspected skin disease, for example) as the predetermined target. The identification by the identification device 100 is performed in order to assist a doctor in making a diagnosis. In an identification based on an image, the identification device 100 does not use two-dimensional image data as it is, but acquires one-dimensional data from the image data, and identifies a predetermined target in the image using the acquired one-dimensional data.

Specifically, the identification device 100 acquires one-dimensional data from image data (training image data) included in a previously prepared set of image data for training, and trains (machine learning) a support vector machine (SVM) using a feature quantity extracted from the one-dimensional data, and performs an image identification using the trained SVM. Since the identification device 100 extracts a feature quantity for training the SVM, the identification device 100 is also a feature quantity extracting device.

A correct label according to a usage of an image identification is given to the training image data. The identification device 100 according to Embodiment 1 performs an identification of whether a mole is benign or malignant based on an image in which the mole is captured as the above-described diagnostic target. Therefore, the training image data is image data including a mole that is already known to be benign or malignant, and each training image data is assigned with a correct label indicating whether the mole in the image is benign or malignant.

Here, the identification device 100 is described as a device for identifying whether a mole is benign or malignant, however, the identification target by the identification device 100 is not limited to a skin disease such as a mole. For example, for cervical cancer, oral cavity cancer (lingual cancer, gum cancer, floor of the mouth cancer) or the like, a disease name and the like of the target can be identified based on an image of the target being the diagnostic target. In this case, the training image data is image data captured of a diagnostic target whose disease name is already known, and each training image data is assigned with a correct label indicating the disease name of the diagnostic target in the image.

Furthermore, the identification target is not limited to a diagnostic target of a human body. An image of another suitable object such as concrete can be used to identify a degradation state of concrete, for example. In this case, the training image data is image data captured of concrete whose presence of degradation is already known, and each training image data is assigned with a correct label with the information of the presence or absence of degradation of the concrete captured in the image. Similarly, in the following embodiments and variations, the identification target is not limited to a diagnostic target area of a human body.

As a functional configuration, the identification device 100 according to Embodiment 1 includes a controller 10, a storage 20, an image inputter 31, an outputter 32, a communicator 33, and an operation inputter 34, as illustrated in FIG. 1.

The controller 10 is configured with a central processing unit (CPU) and the like, and realizes a function of each section (an acquirer 11, a specifier 12, an extractor 13, a setter 14, an identifier 15) described later by executing a program stored in the storage 20.

The storage 20 is configured with a read only memory (ROM), Random Access Memory (RAM) and/or the like, and stores a program executed by the CPU of the controller 10 and necessary data. The storage 20 also stores image data (training image data) for training the identifier 15. However, the identification device 100 may acquire all or part of the training image data from the communicator 33.

The image inputter 31 is a device for inputting training image data and image data of an (unknown) identification target given by a user. The image inputter 31 is a camera, for example, and inputs captured image data to the controller 10. An image used by the identification device 100 when identifying a predetermined target is an image that contains a plurality of regions where at least one of colors and luminance is mutually different. Therefore, the image inputter 31 inputs an image including a plurality of regions where at least one of colors and luminance is mutually different to the controller 10. The plurality of regions where at least one of colors and luminance is mutually different includes an edge region and other regions of an image, for example.

The image inputter 31 is not limited to a camera, but can be any device as long as the controller 10 can acquire image data. For example, when image data is stored in the storage 20, and the controller 10 acquires the image data by reading it from the storage 20, the storage 20 serves as the image inputter 31. When the controller 10 acquires image data from an external server or the like via the communicator 33, the communicator 33 serves as the image inputter 31.

The outputter 32 is a device for the controller 10 to output an image identification result and the like. For example, the outputter 32 is a liquid crystal display or an organic electro-luminescence (EL) display. The identification device 100 may include such a display as the outputter 32, or may include an outputter 32 as an interface for connecting an external display. When the identification device 100 includes an outputter 32 as an interface, an image identification result and the like are displayed on an external display that is connected via the outputter 32.

The communicator 33 is a device (network interface or the like) for transmitting and receiving data to and from another external device (a server or the like storing a database for image data, for example). The controller 10 can acquire image data via the communicator 33.

The operation inputter 34 is a device for accepting a user operation input to the identification device 100 such as a keyboard, a mouse, and a touch panel, for example. The identification device 100 accepts an instruction and the like from a user via the operation inputter 34.

Functions of the controller 10 will be described. The controller 10 realizes functions of the acquirer 11, the specifier 12, the extractor 13, the setter 14, and the identifier 15.

The acquirer 11 acquires an image captured by the image inputter 31. As described above, the image used by the identification device 100 when identifying the predetermined target is the image that contains the plurality of regions where at least one of colors and luminance is mutually different, and the acquirer 11 acquires the captured image of the predetermined target (an area of skin being a diagnostic target such as a mole) including such regions. The acquirer 11 does not need to acquire the captured image in real time, but may acquire, for example, the captured image that has been captured in the past and stored in the storage 20, or may receive and acquire the captured image that has been captured in the past and stored in another server or the like via the communicator 33. The acquirer 11 functions as acquiring means for acquiring the captured image.

Figure 2:
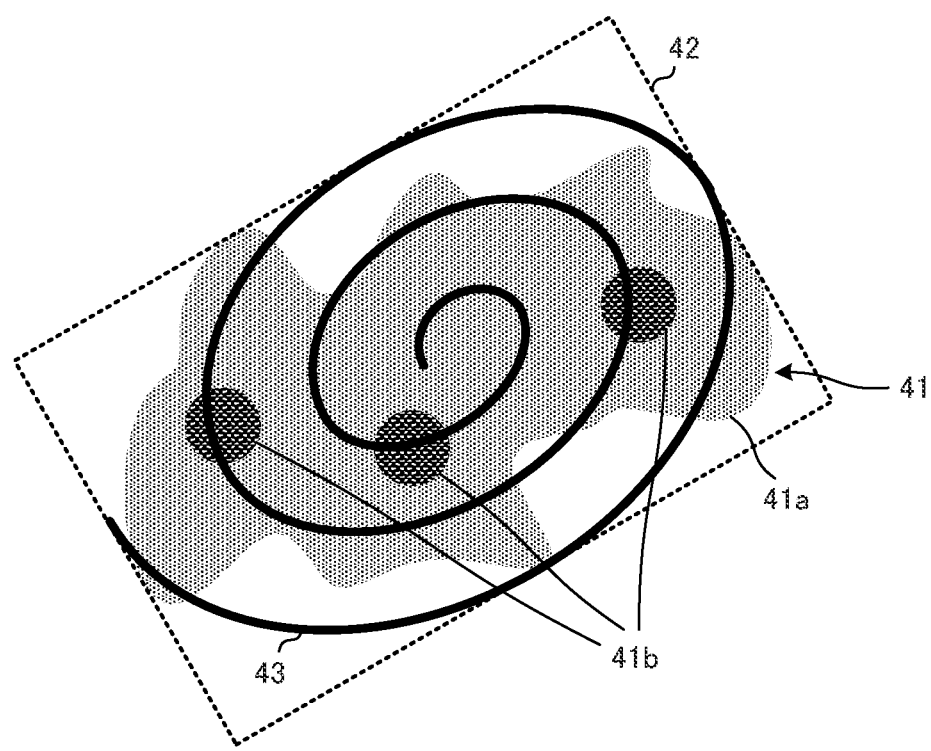
FIG. 2 is a diagram illustrating a linear region specified by a specifier according to Embodiment 1.

The specifier 12 specifies a linear region extending in a plurality of mutually different directions, from a region to be identified of the captured image acquired by the acquirer 11. The region to be identified includes a predetermined target (diagnostic target or the like of skin). The line extending in a plurality of mutually different directions is a plurality of lines extending in mutually different directions (for example, a plurality of lines extending radially from a vicinity of the center of the predetermined target), or a line whose local regions are oriented in a plurality of different directions (a circle, an oval, a spiral curve or the like). Here, "a local region on the line" is a portion of the line (small line segment) on various positions. For example, the specifier 12 specifies a linear region where a spiral curve 43 passes through a region to be identified 42 including a target region 41 being the diagnostic target of skin (a part suspected to be a diseased part), as illustrated in FIG. 2. The target region 41 includes a plurality of regions 41a and 41b where at least one of colors and luminance is mutually different. The specifier 12 functions as specifying means for specifying such the linear region.

Figure 3:
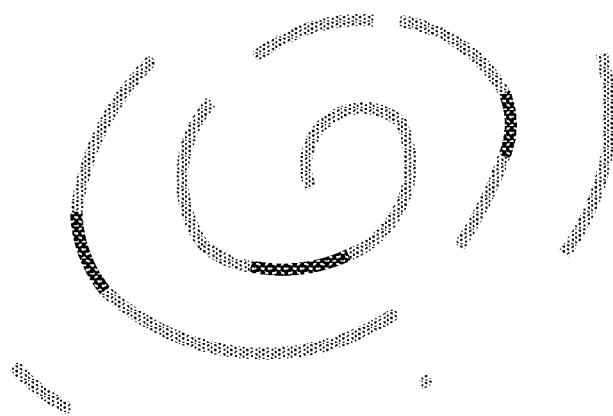
FIG. 3 is a diagram illustrating an example of acquiring a pixel value along a curved line.
Figure 4:
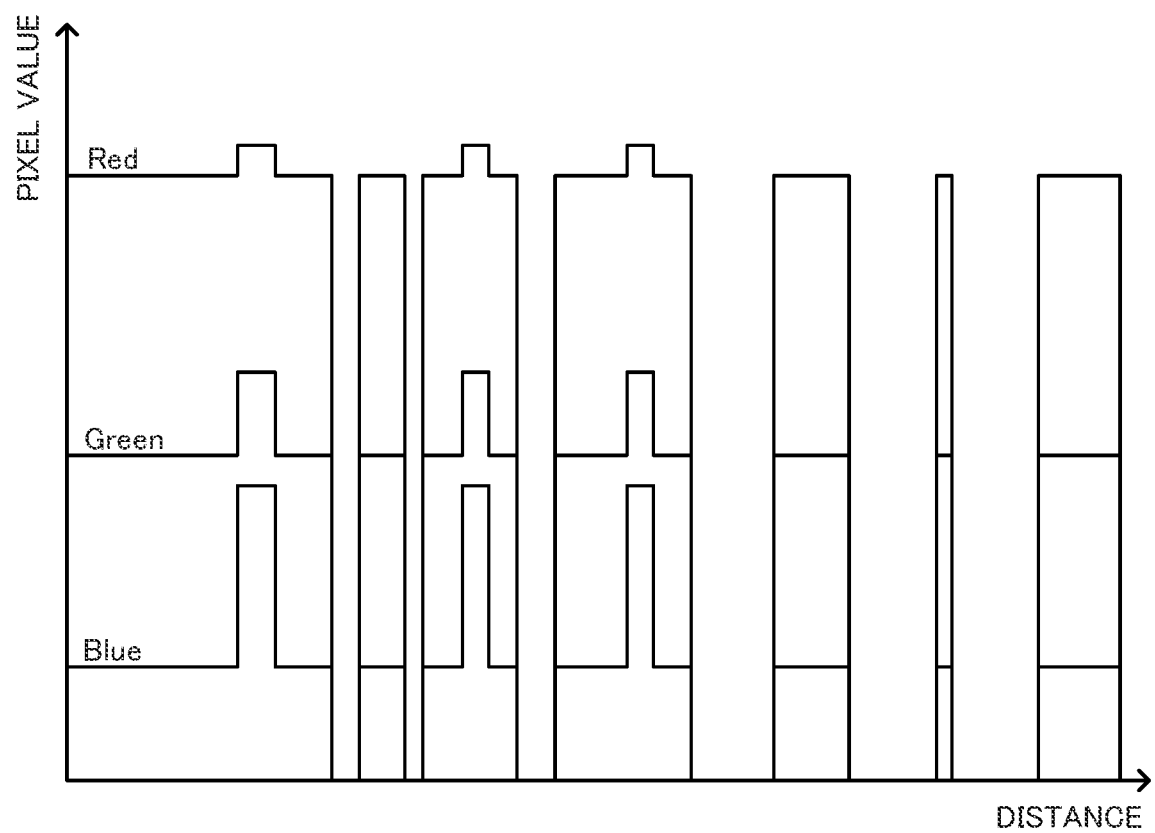
FIG. 4 is a diagram illustrating an example of acquired one-dimensional data.

The extractor 13 extracts a feature quantity based on a pixel value, from the linear region specified by the specifier 12. In more detail, the extractor 13 first acquires one-dimensional data configured by acquiring pixel values (each of RGB values) in order along the (one-dimensional) spiral curve 43 that passes through the region specified by the specifier 12, from an end to the other end of the spiral curve 43, as illustrated in FIG. 3. Here, the pixel values are expressed by R (Red) component, G (Green) component, and B (Blue) component in the RGB color space, and the acquired one-dimensional data is one-dimensional data of three channels (Red, Green and Blue, respectively), as illustrated in FIG. 4. In FIG. 4, the horizontal axis is labeled "distance", and the "distance" in FIG. 4 means "the distance from an end of the spiral curve when viewed along the spiral curve". This one-dimensional data may be appended with additional information such as time information indicating the time when the image is captured, patient ID information indicating which patient the captured image belongs to, and doctor ID information indicating a doctor of the patient.

The extractor 13 calculates predetermined statistic values for the one-dimensional data of the acquired R component, G component and B component such as a mean, variance, a maximum value, a minimum value, a median, a gradient of a regression line (a straight line approximating one-dimensional data with a linear function, which can be acquired by the least-squares method or the like), a contribution ratio of the regression line (a measure of how well the observed one-dimensional data of RGB components are replicated by the regression line, also referred to as a coefficient of determination) and the like, for example. The extractor 13 also treats the differences among RGB components (R component–G component, R component–B component, G component–B component) and ratios (R component/G component, R component/B component, G component/B component) as the respective one-dimensional data, and calculates the predetermined statistics values (a mean, variance and the like) described above.

The extractor 13 calculates, for example, a total of the following 16 values as the feature quantity: variance of the one-dimensional data of each of the R component and G component, the gradient and the contribution ratio of the regression line of the one-dimensional data of each of RGB components, variance of absolute values of the differences of the one-dimensional data of each of RGB components being differences of RGB components (R component–G component, R component–B component, G component–B component), the gradients and the contribution ratios of the regression lines of the R component/G component and R component/B component among the ratios of one-dimensional data of each of RGB components (ratios of RGB components (R component/G component, R component/B component, G component/B component)), the difference between the maximum value and the minimum value in each of the one-dimensional data of RGB components (the differences between the maximum values in the RGB components and the minimum values in the RGB components). In other words, in this example, the feature quantity is expressed by a 16-dimensional vector. The extractor 13 functions as extracting means for extracting the feature quantity.

Here, the extractor 13 has been described as acquiring each pixel value as a value of each of R component, G component, and B component in the RGB color space, however, the color space representing the pixel values is not limited to the RGB color space. For example, YUV color space, Lab color space or the like can be utilized. Since all of these color spaces express one pixel value in three components, the R component, Y component and the L component can be represented as a first component in each color space, the G component, U component, and a component can be represented as a second component in each color space, and the B component, V component, and b component can be represented as a third component in each color space.

Then, the extractor 13 may acquire pixel values in the linear region specified by the specifier 12 as one-dimensional data of each of the first component, second component, and third component in the above-described arbitrary color space, and may extract, as a feature quantity, at least one of the total of 16 values being the variance of one-dimensional data of the first and second components, respectively, the gradients and the contribution ratios of the regression lines of the one-dimensional data of the first, second and third components, respectively, variance of absolute values of differences among the one-dimensional data, gradients and contribution ratios of the regression lines of the first component/the second component, and the first component/the third component among the ratios of the one-dimensional data, and the differences of the maximum values and the minimum values of the one-dimensional data.

The setter 14 randomly sets parameters that define a spiral curve that passes through a region specified by the specifier 12. The parameters are, for example, a type of the spiral curve (an Archimedean spiral, a radiated spiral, or the like. An Archimedean spiral in FIG. 2), a number of turns of the spiral curve (three turns in FIG. 2), a direction (clockwise from the inside to the outside in FIG. 2), a start angle (90-degree vertical direction with respect to a rectangle of the region to be identified 42 in FIG. 2), and/or the like. The setter 14 functions as setting means for randomly setting parameters that define the spiral curve of the spiral-curve-shaped region.

The identifier 15 identifies the predetermined target (such as a diagnostic target on skin) using the feature quantity extracted by the extractor 13. Specifically, the identifier 15 is an SVM that has machine-learned using the feature quantity extracted by the extractor 13 from the training image data. Here, the identifier 15 includes an SVM for identifying whether a mole is benign or malignant because the identification device 100 is a device for identifying whether a mole on skin is benign or malignant. The identifier 15 identifies whether the mole is benign or malignant based on an output value obtained by inputting the feature quantity to the SVM as input data. In other words, when the output value of the SVM is a value indicating benignity, the identification result of the identifier 15 is benign, and when the output value of the SVM is a value indicating malignancy, the identification result of the identifier 15 is malignant.

In the present embodiment, the identification device 100 is described as a device for identifying whether a mole is benign or malignant, however, the content of an identification by the identification device 100 is not limited to the benignity/malignancy of a mole, moreover, the identification target is not limited to a mole. The identification device 100 may identify a disease name (pigmented naevus (mole), melanoma, seborrheic keratosis, and the like) of a skin disease. In this case, the identifier 15 includes number of SVMs for one-to-multiple identification equal to the number of classes to be identified. For example, when the identification device 100 identifies three diseases of pigmented naevus (mole), melanoma, and seborrheic keratosis, the identifier 15 includes three SVMs being an SVM for identifying a pigmented naevus (mole), an SVM for identifying a melanoma, and an SVM for identifying a seborrheic keratosis. The feature quantity is input to the three SVMs, and a disease name corresponding to the SVM which outputs the most probable result becomes the identification result of the identifier 15.

As a more general description, for example, when n classes of A, B, C, . . . exist as the identification target by the identification device 100, the identifier 15 includes n SVMs being an SVM for identifying "A or other than A", an SVM for identifying "B or other than B", an SVM for identifying "C or other than C", and so forth. The feature quantity is input to the n SVMs, and a class (A, B, C, . . . ) corresponding to the SVM which outputs the most probable result becomes the identification result of the identifier 15. The identifier 15 functions as identification means for identifying the predetermined target (such as a diagnostic target on skin).

The functional configuration of the identification device 100 has been described. Next, a learning process of the identification device 100 will be described with reference to FIG. 5. The learning process starts when a user instructs the identification device 100 to start the learning process via the operation inputter 34.

The acquirer 11 acquires training image data from the storage 20 (step S101). The step S101 is also referred to as an acquiring step. Then, the specifier 12 extracts the target region 41 that includes the predetermined target (an area of skin being the diagnostic target such as a mole) from the training image data acquired by the acquirer 11 (step S102).

The extraction of the target region 41 in the step S102 may be performed automatically using a deep neural network (DNN) or the like being a fully convolutional networks (FCN) trained with a lesion region (in this case, a mole), or may be performed semi-automatically using a technique such as an interactive graph cut method, or may be performed manually by a user specifying the target region 41 using the operation inputter 34, or the like.

Then, the specifier 12 calculates the region to be identified 42 being a rectangle surrounding the extracted target region 41 (step S103). For example, the specifier 12 calculates the region to be identified 42 as a rectangle with a major diameter of the maximum diameter of any two points inside the extracted target region 41, and with a minor diameter defined in such a way that the target region 41 is inscribed therein, in a direction orthogonal to the major diameter, as illustrated in FIG. 2.

Then, the setter 14 sets random values as the parameters that define the spiral curve (a type of the spiral curve, a number of turns of the spiral curve, a direction, and a start angle) that passes through the region to be identified 42 calculated by the specifier 12 (step S104). For example, the type of the spiral curve is randomly set from an Archimedean spiral, a radiated spiral, and the like. The number of turns of the spiral curve is randomly set from about two to six turns, for example. Any number may be set as the number of turns, and the number may be greater than the six mentioned above. The number of turns may not be an integer, and 3.5, 3.25 turns or the like may be set. The direction of the spiral curve is randomly set as either clockwise or counterclockwise. The starting angle of the spiral curve may be any angle, however, for example, candidate angles such as 0, 90, 180, 270 degrees may be selected, and one of the candidates may be randomly set.

Then, the specifier 12 defines a spiral curve in such a way that the center of the spiral curve substantially coincides with the center of the region to be identified 42, and the spiral curve inscribes to the region to be identified 42, using the spiral curve parameters set by the setter 14, as illustrated in FIG. 2 (step S105). The step S105 is also referred to as a specifying step because it specifies the linear region extending in the plurality of mutually different directions from the region to be identified 42. The center of the spiral curve may or may not perfectly coincide with the center of the region to be identified 42. When the center of the spiral curve is shifted from the center of the region to be identified 42, a distance and a direction of the center of the spiral curve to be shifted may be randomly set. Moreover, the distance and the direction to shift the center of the spiral curve from the center of the region to be identified 42 may be a part of the "parameters that define the spiral curve" set in the step S104. When the distance and the direction to be shifted are the part of the "parameters that define the spiral curve", the training is performed in a more variety of spiral curves, potentially leading to improved accuracy of the identifier 15.

Then, the extractor 13 obtains pixel values along the spiral curve defined by the specifier 12 as illustrated in FIG. 3, and obtains one-dimensional data of each of RGB components, as illustrated in FIG. 4 (step S106). The pixel values may be acquired by adding a new pixel value to the one-dimensional data every time a pixel changes along the spiral curve, or may be acquired by adding, every time a predetermined distance is traveled along the spiral curve, a pixel value of the place to the one-dimensional data. The color space may be a color space other than the RGB color space (YUV color space, Lab color space, or the like), as described above. When a color space other than the RGB color space is utilized, the extractor 13 converts color spaces when acquiring one-dimensional data. For example, when the RGB color space is converted to the YUV color space, the extractor 13 acquires one-dimensional data of each of a Y component, a U component, and a V component.

The extractor 13 may fix the size of the one-dimensional data (number of pixel values to obtain) acquired in the step S106. When the size is fixed, the extractor 13 linearly interpolates the one-dimensional data, and adjusts the size to a predetermined size.

Then, the extractor 13 extracts the feature quantity (the above-described 16-dimensional vector, for example) by calculating a mean and variance and the like for the acquired one-dimensional data, and by calculating a mean and variance and the like for the differences and ratios of the components, and stores the feature quantity in the storage 20 with the correct label assigned to the training image data (step S107). The step S107 is also referred to as an extracting step.

Then, the controller 10 determines whether the process from the step S104 to the step S107 has been iterated for predetermined number of times (10 times, for example) or not (step S108). When the process has not been iterated (step S108; No), the process returns to the step S104. By repeating the process for the predetermined times, the variety of the parameters of the spiral curve randomly set in the step S104 increases, and therefore robustness of the training of the SVM of the identifier 15 can be increased because a feature quantity can be extracted based on one-dimensional data along various shapes of spiral curves. The robustness of the training of the SVM of the identifier 15 can also be increased by increasing the number of the training image data. Therefore, when a very large number (10,000 or more, for example) of pieces of training image data can be prepared, the predetermined number of times of iterations in the step S108 may not be necessary (the process of the step S108 may be skipped, and the step S109 may be processed immediately).

When the process has been repeated for the predetermined number of times (step S108; Yes), the controller 10 determines whether the process from the step S103 to the step S108 has been performed for all of the target regions in the training image data (step S109). The objective is to extract a feature quantity for training for all of the target regions when a plurality of target regions exists in one piece of training image data. When the process from the step S103 to the step S108 has not been performed for all of the target regions (step S109; No), the process returns to the step S103.

When the process from the step S103 to the step S108 has been performed for all of the target regions (step S109; Yes), the controller 10 determines whether the feature quantities have been extracted for all of the training image data (step S110). When the feature quantities have not been extracted for all of the training image data yet (step S110; No), the process returns to the step S101.

Figure 5:
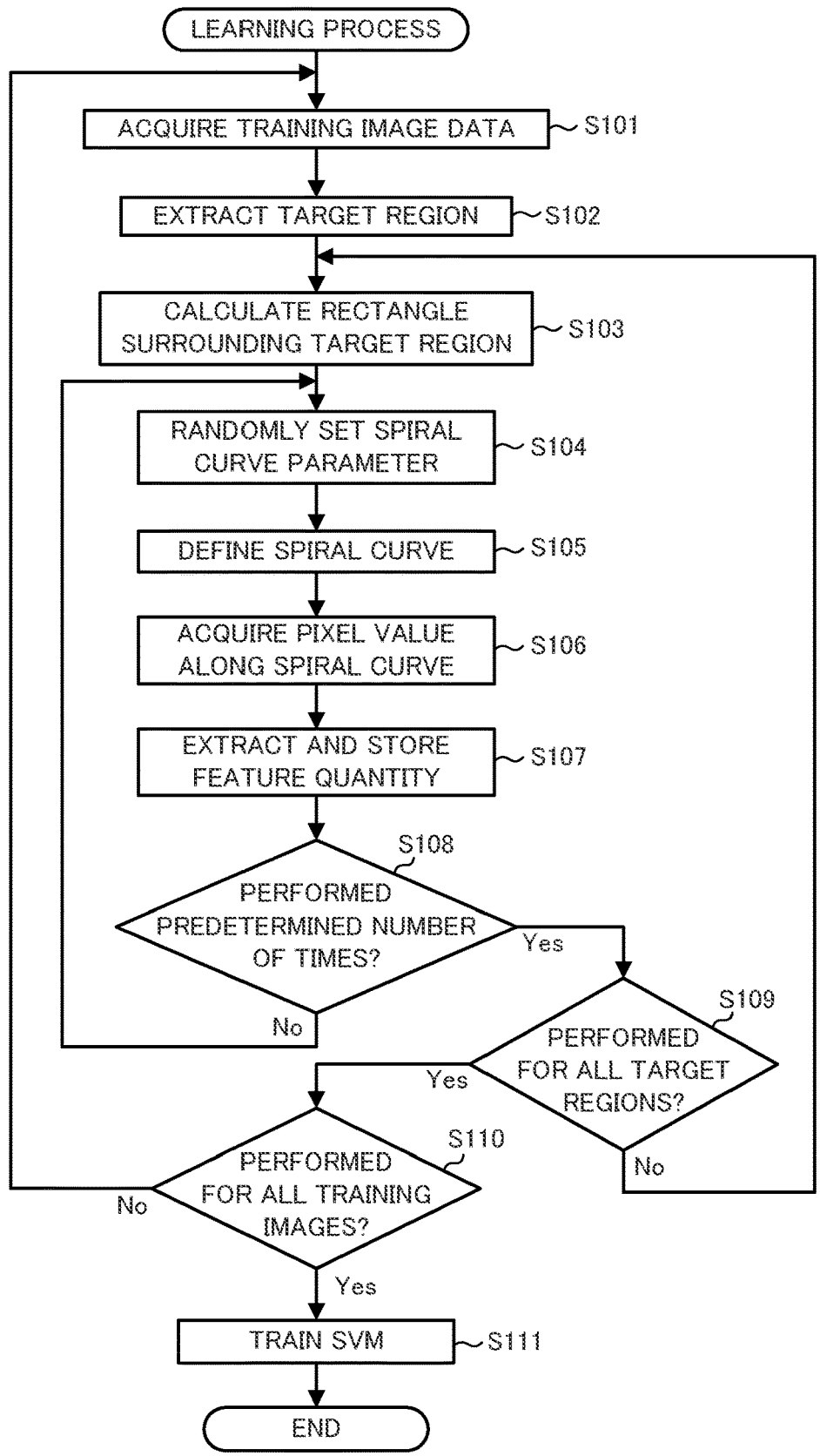
FIG. 5 is a flowchart of a learning process according to Embodiment 1.

When the feature quantities have been extracted for all of the training image data (step S110; Yes), the SVM of the identifier 15 is trained with the feature quantities and the correct labels stored in the storage 20 in the step S107 (step S111), and the learning process is terminated. The flow chart illustrated in FIG. 5 is merely an example, and the order of the process and the content of the process may be modified in order to increase training efficiency and identification performance.

The learning process has been described above. Next, an identification process for identifying an image using the identifier 15 (SVM) trained in the above-described learning process will be described with reference to FIG. 6. The identification process starts when a user instructs the identification device 100 to start the identification process via the operation inputter 34.

The acquirer 11 acquires an image to be identified from the image inputter 31 or the like (step S201). The step S201 is also referred to as an acquiring step. For example, the acquirer 11 acquires the image to be identified when a user captures an image he or she wants to be identified using the image inputter 31.

Then, the specifier 12 extracts the target region 41 that includes the predetermined target (an area of skin being a diagnostic target such as a mole) from the image to be identified acquired by the acquirer 11 (step S202). The extraction of the target region 41 in the step S202 may be performed automatically, semi-automatically, or manually, similarly to the step S102.

Then, the specifier 12 calculates the region to be identified 42 being a rectangle surrounding the extracted target region 41 (step S203). For example, the specifier 12 calculates the region to be identified 42 as a rectangle with a major diameter of the maximum diameter of any two points inside the target region 41, and with a minor diameter defined in such a way that the extracted target region 41 is inscribed therein, in a direction orthogonal to the major diameter, as illustrated in FIG. 2.

Then, the specifier 12 sets typical values (for example, a type of a spiral curve: Archimedean spiral, a number of turns of the spiral curve: 3, a direction: clockwise, and a start angle: vertical 90-degree direction, as illustrated in FIG. 2) for parameters that define the spiral curve that passes through the calculated region to be identified 42 (the type of the spiral curve, the number of turns of the spiral curve, the direction, and the start angle), and by using the set parameters, defines the spiral curve in such a way that the center thereof coincides with the center of the region to be identified 42, and the spiral curve is inscribed in the region to be identified 42 (step S204). The step S204 is also referred to as a specifying step because it specifies a linear region extending in a plurality of mutually different directions from the region to be identified 42. In the step S204, instead of setting typical values as the parameters defining the spiral curve, the specifier 12 may randomly set these parameters.

Then, the extractor 13 obtains pixel values along the spiral curve defined by the specifier 12 as illustrated in FIG. 3, and obtains one-dimensional data of each of RGB components, as illustrated in FIG. 4 (step S205). The step S205 is also referred to as a one-dimensional data acquiring step. In the step S205, the extractor 13 functions as one-dimensional data acquiring means. The unit of pixel value acquisition and the color space to be used are the same as the ones used in the learning process (FIG. 5, step S106). When the size of the one-dimensional data has been fixed in the learning process, the extractor 13 linearly interpolates the one-dimensional data, and adjusts the size to the one that has been used in the learning process.

Then, the extractor 13 extracts the feature quantity (the above-described 16-dimensional vector, for example) by calculating the mean and variance and the like for the acquired one-dimensional data, and by calculating the mean and variance and the like for the differences and ratios of the components (step S206).

Then, the identifier 15 identifies the predetermined target (a mole) included in the target region extracted in the step S202, by inputting the feature quantities extracted in the step S206 to the SVM trained in the learning process in FIG. 5 (step S207). The step S207 is also referred to as an identifying step. Then, the controller 10 outputs the result identified by the identifier 15, in other words, whether the mole is a benign mole or a malignant mole to the outputter 32 (step S208), and the identification process is terminated.

The identification process has been described above. As described above, since the identification device 100 according to Embodiment 1 utilizes one-dimensional data when extracting the feature quantity from the image, the processing load can be reduced than a case where two-dimensional image data is handled directly. In other words, the identification device 100 can perform a fast image identification on its own without utilizing external computer resources. Therefore, the identification device 100 can be utilized when cloud-based processing (computer resources such as a server on the Internet) is not available, when a large number of images need to be identified (image screening and the like, for example), when the identification needs to be performed in real time, and the like.

Moreover, the total number of prepared pieces of image data for training can be fewer because the identification device 100 can acquire more training data (one-dimensional data) from one image by changing parameters of a line (a spiral curve) used when acquiring the one-dimensional data than training directly with a two-dimensional image.

Figure 6:
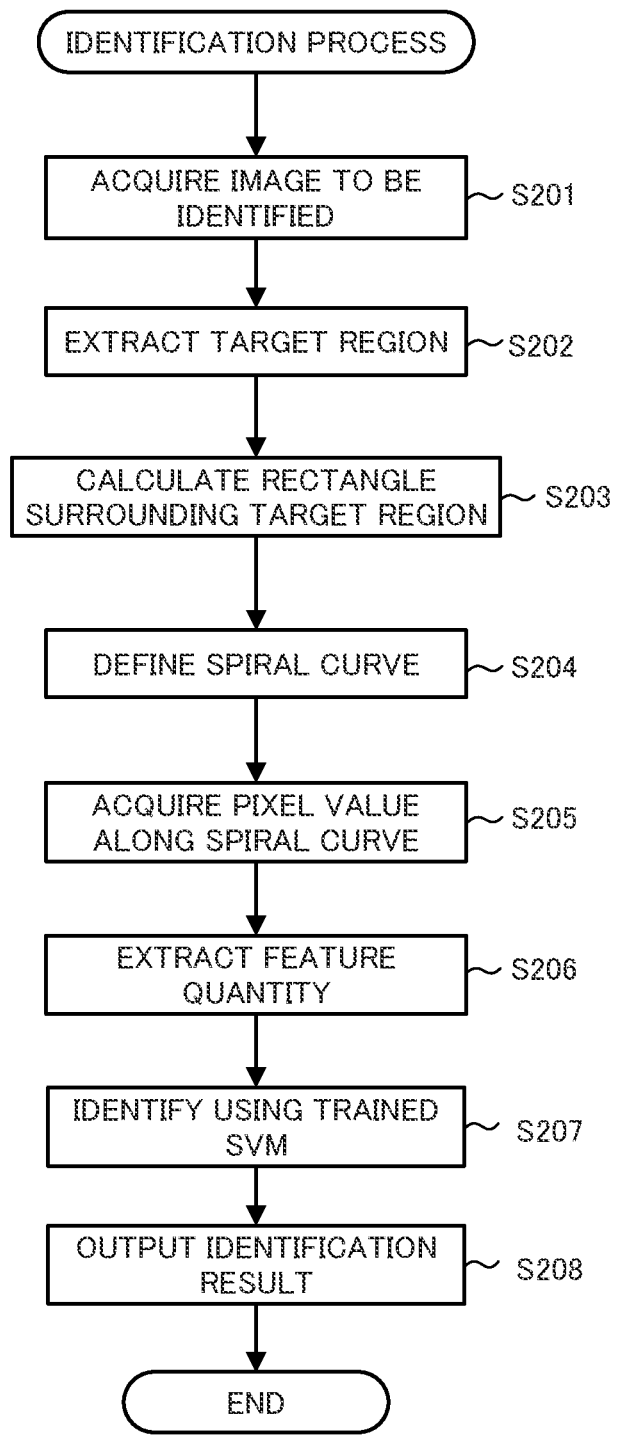
FIG. 6 is a flowchart of an identification process according to Embodiment 1.

In the above-described Embodiment 1, a linear identification is performed by the SVM, however, a non-linear identification can also be performed by using an SVM adapted for a non-linear identification using a kernel method or the like in the step S111 in the learning process (FIG. 5) and the step S207 in the identification process (FIG. 6). The identification can also be performed by setting a threshold value for each dimension of the feature quantity, expressing the feature quantity in a binary vector indicating whether a component in each dimension is equal to or above, or below the threshold value, and performing a non-linear scoring of the computation result by this binary vector.

Embodiment 2

The identification device 100 according to Embodiment 1 performs an identification with an SVM using the predefined feature quantity. However, by applying DNN such as Convolutional Neural Network (CNN) to the above-described one-dimensional data, identification can be performed without the predetermining feature quantity (calculation method of each component of a feature quantity vector and the like). An identification device 101 according to Embodiment 2 operating in the above-described manner will be described.

The identification device 101 according to Embodiment 2 has the same functional configuration as that of the identification device 100 according to Embodiment 1 illustrated in FIG. 1, however, the identifier 15 is a CNN instead of an SVM, and the extractor 13 machine-trains the CNN by updating the weight and the like inside the CNN of the identifier 15. As a result, the extractor 13 becomes able to extract an output value of the CNN or a feature map inside the CNN as the feature quantity.

The CNN utilized in the identification device 101 according to Embodiment 2 will be described. A CNN is a neural network that emulates a function of nerve cells in a human visual cortex, and usually performs an image identification and the like by directly handling two-dimensional image data. However, the CNN according to Embodiment 2 is a one-dimensional convolutional neural network that accepts one-dimensional data in RGB (3-channel) as input data, and performs an N-class identification by processing the one-dimensional data as it is, as illustrated in FIG. 7.

Figure 7:
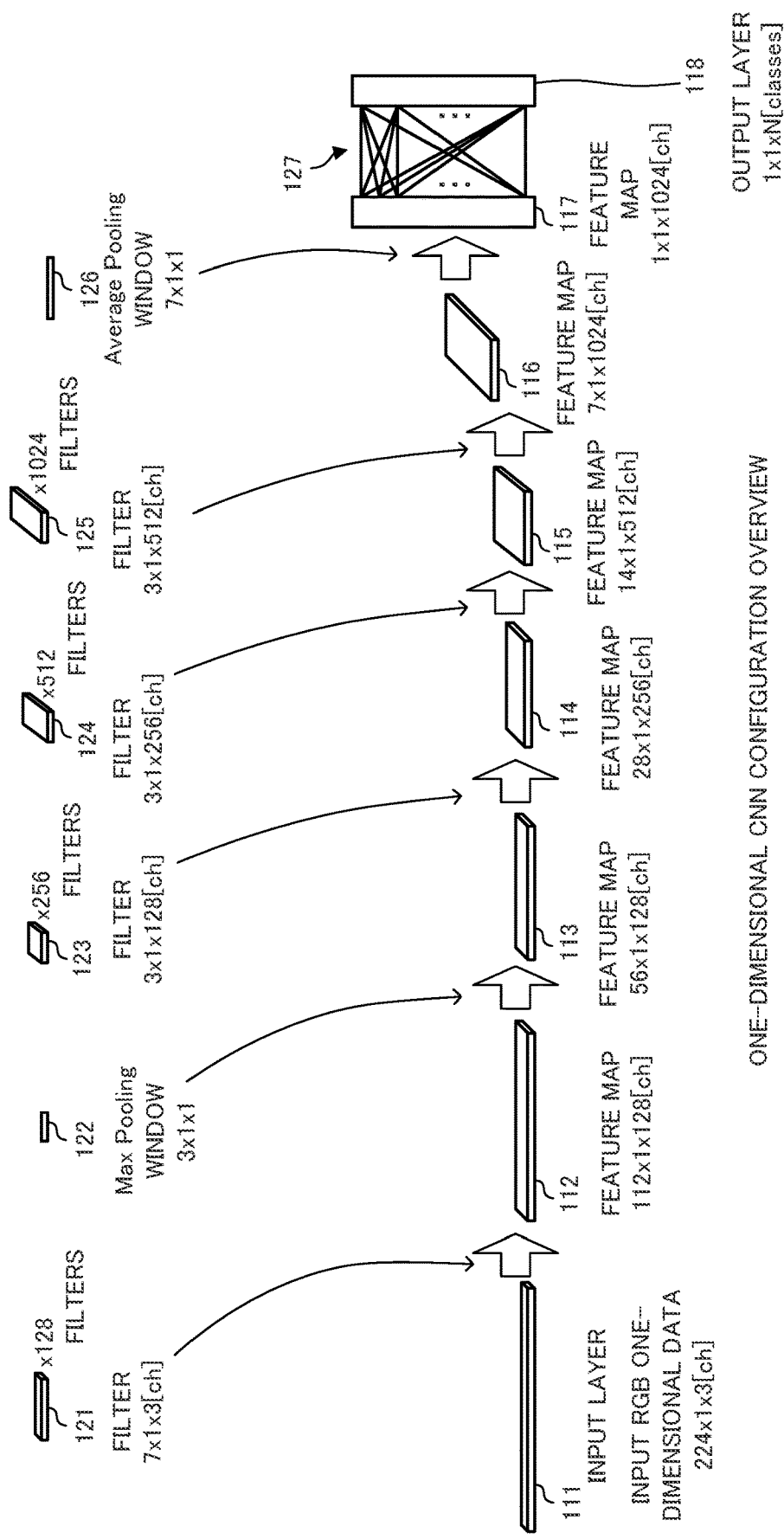
FIG. 7 is a diagram illustrating an overview of a configuration of a one-dimensional CNN according to Embodiment 2.

As illustrated in FIG. 7, the CNN according to Embodiment 2 performs one-dimensional convolution processing (filter scanning) and pooling processing (window scanning) to an input layer 111 that accepts one-dimensional RGB data in order to acquire feature maps 112, 113, 114, 115, 116 and 117 with gradually decreasing sizes, and finally obtains an N-dimensional output vector from an output layer 118. In an example illustrated in FIG. 7, by scanning the input one-dimensional data with filters for convolution processing 121, 123, 124 and 125 and filters for pooling processing 122 and 126 horizontally with a stride of two, feature maps of gradually decreasing sizes are calculated, and a final output is obtained. To scan with a stride of two means to scan by skipping one pixel or a component configuring the feature map at a time.

Weight factors are assigned to each component of the filters 121, 123, 124, and 125, and by scanning in a horizontal direction on the input one-dimensional data or the feature map having the same number of channels, an inner product of scalar value is output on each attention point on the input one-dimensional data or the feature map, and therefore a new feature map can be obtained. By applying a plurality of filters (n number of filters), the same number of feature maps (n channels) are obtained. The horizontal size of the feature map becomes ½ the size every time scanning is performed with a stride of two. As a result, as the process proceeds to later steps, a more global feature extraction is performed (the filter size expands relative to the feature map size).

In the example illustrated in FIG. 7, the last layer of the intermediate layer of the CNN (feature map 117) and the output layer 118 are connected by a full connection 127 assigned with weight factors, and a weighted addition is performed similarly to a standard neural network. The last layer of intermediate layers of the CNN is also referred to as a fully connected layer since it is connected to the output layer 118 by a full connection 127. In this example, since an identification of N classes is performed, the output layer 118 includes N elements (or units), and the magnitudes of the values of the elements represent the magnitudes of probabilities of the estimated identification.

In the CNN, weight factors assigned to each connection in the full connection 127 and weight factors of the above-described filters 121, 123, 124, 125 can be obtained by using previously prepared training data. Specifically, the training data is input as an input image to the input layer 111, and the data is propagated in a forward direction, and an output result is obtained from the output layer 118. Then, the extractor 13 calculates a difference (an error) between the output result and a correct answer (a correct label assigned to the input training data), and updates the weight factors to reduce the error using an error back propagation method. By performing this operation repeatedly while reducing a learning rate (amount of updating the weight factors in the error back propagation method), the values of the weight factors converge.

After training each CNN weight factor with the training data, by forward propagating unknown image data as input image data, the output layer 118 can output a result being an estimation of the identification based on the input image. The output result is the identification result by the identifier 15.

An overview of the one-dimensional CNN included in the identifier 15 of the identification device 101 has been described above. The CNN illustrated in FIG. 7 is merely an example of a one-dimensional CNN. The identification device 101 may utilize any one-dimensional CNN as long as it is a CNN (one-dimensional CNN) whose input layer accepts one-dimensional data and processes the one-dimensional data as it is.

Figure 8:
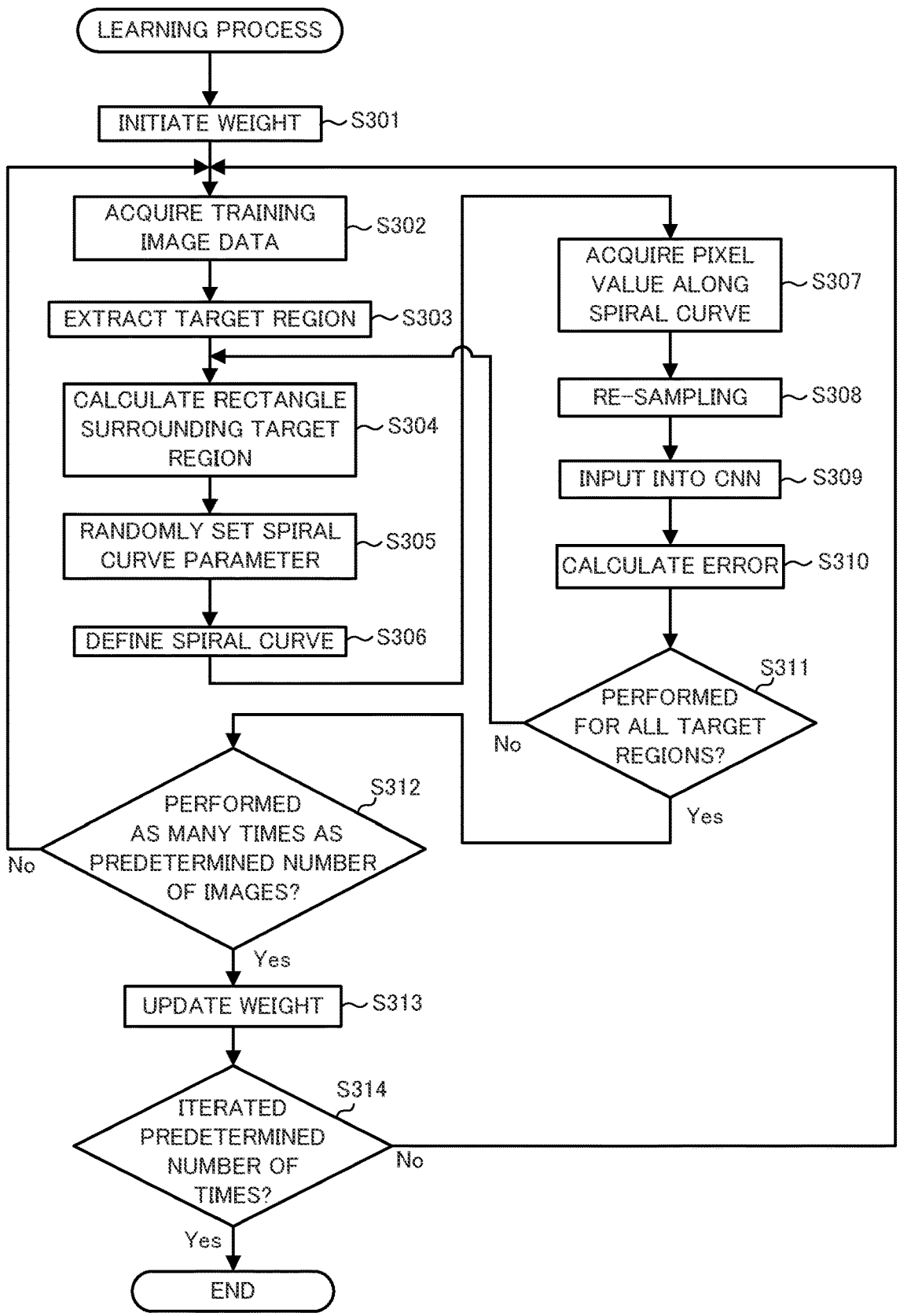
FIG. 8 is a flowchart of a learning process according to Embodiment 2.

Next, a learning process performed by the identification device 101 will be described with reference to FIG. 8. The learning process starts when a user instructs the identification device 101 to start the learning process via the operation inputter 34.

Firstly, the extractor 13 initializes all the weight parameters in the CNN of the identifier 15 (step S301). Since the following steps from S302 to S307 are the same as the steps from S101 to S106 of the learning process (FIG. 5) of Embodiment 1, the description thereof is omitted.

Then, the extractor 13 adjusts the size of the one-dimensional data of the pixel values (RGB, YUV, Lab or the like depending on the color space to be used) obtained in the step S307 by re-sampling using linear interpolation to fit the size of the input layer of the CNN of the identifier 15 (224 in the example in FIG. 7) (step S308).

Then, the extractor 13 inputs the re-sampled one-dimensional data to the CNN of the identifier 15 (step S309), and obtains an output from the CNN. Then, the extractor 13 calculates an error between the output from the CNN and the correct label assigned to the training image data (step S310), and stores the error in the storage 20.

The controller 10 determines whether the process from the step S304 to the step S310 has been performed for all of the target regions in the training image data (step S311). The objective is to input and train the CNN for all of the target regions when a plurality of target regions exists in one piece of training image data. When the process from the step S304 to the step S310 has not been performed for all of the target regions (step S311; No), the process returns to the step S304.

When the process from the step S304 to the step S310 has been performed for all of the target regions (step S311; Yes), the controller 10 determines whether the process from the step S302 to the step S311 has been repeated as many times as the predetermined number of pieces of the training image data (also referred to as a batch size, 50, for example) (step S312). When the process has not been iterated as many times as the predetermined number of the pieces of the training image data (S312; No), the process returns to the step S302. The iterative process for the number of times of the batch size is referred to as a mini-batch.

When the process has been repeated as many times as the predetermined number of the pieces of the training image data (step S312; Yes), the extractor 13 updates the weight parameters in the CNN in the identifier 15, based on an average of the errors stored in the storage 20 in the step S310 until that time (step S313). The step S313 is also referred to as an extracting step because the step S313 can be considered as a step for extracting the feature quantity in the training image data to the inside of the CNN. Then, the controller 10 determines whether the process from the step S302 to the step S313 has been iterated for a predetermined number of times (for example, a number obtained by dividing the number of the pieces of the training image data by a batch size and multiplying by a predetermined number (also referred to as an epoch number, 100, for example)) or not (step S314).

When the process from the step S302 to the step S313 has not been performed for the predetermined number of times (step S314; No), the process returns to the step S302. When the process has been iterated for the predetermined number (step S314; Yes), the learning process is terminated. In the learning process (FIG. 8) according to Embodiment 2, compared to the learning process (FIG. 5) according to Embodiment 1, a determination content in iterating the process and a position of the iteration are slightly different. The reason is that, when training a CNN, when the same training image data is used iteratively in the same mini-batch, the CNN may be overtrained. However, the flow chart in FIG. 8 is merely an example, and the order of the process and the content of the process may be modified in order to increase training efficiency and identification performance. For example, in the learning process (FIG. 8) according to Embodiment 2, the process from the step S305 to the step S310 may be iterated for a predetermined number of times, similarly to the step S108 of the learning process FIG. 5 according to Embodiment 1. The reason is that, in the step S305, since random spiral curve parameters are used every time, even when the same training data is used iteratively, an overtraining may be avoided, and the iteration may contribute to an improvement of the identification performance.

The learning process has been described above. Next, an identification process for identifying an image using the identifier 15 (CNN) trained in the above-described learning process will be described with reference to FIG. 9. The identification process starts when a user instructs the identification device 101 to start the identification process via the operation inputter 34.

Since the following step from S401 to the step S405 are the same as the step from S201 to the step S205 of the identification process (FIG. 6) of Embodiment 1, the description thereof is omitted. The extractor 13 adjusts the size of the one-dimensional data of the pixel values (RGB, YUV, Lab or the like depending on the color space to be used) obtained in the step S405 by re-sampling using linear interpolation to fit the size of the input layer of the CNN of the identifier 15 (step S406).

Then, the extractor 13 inputs the re-sampled one-dimensional data to the CNN of the identifier 15 (step S407). The identifier 15 acquires an output value of the CNN as an identification result (step S408). The step S408 is also referred to as an identifying step. Then, the controller 10 outputs the result identified by the identifier 15 to the outputter 32 (step S409), and the identification process is terminated.

The identification process has been described above. As described above, in the identification device 101 according to Embodiment 2, the CNN automatically extracts the feature quantity by simply inputting the one-dimensional data into the CNN. Therefore, the feature quantity (the calculation method of each element of the feature quantity vector and the like) does not need to be previously determined, unlike the identification device 100.

Moreover, in the identification device 101, since one-dimensional data is input into the CNN, the processing load can be reduced than a standard CNN that handles two-dimensional data. In other words, the identification device 101 can perform fast image identification on its own without utilizing external computer resources. Therefore, similarly to the identification device 100, the identification device 101 can be utilized when cloud-based processing (computer resources such as a server on the Internet) is not available, when a large number of images need to be identified (image screening and the like, for example), when the identification needs to be performed in real time, and the like.

Moreover, similarly to the identification device 100, the total number of pieces of image data to prepare for training can be fewer because the identification device 101 can acquire more training data (one-dimensional data) from one image by changing parameters of a line (a spiral curve) used when acquiring the one-dimensional data than training directly with a two-dimensional image.

In order to compensate for the lack of training data, a standard two-dimensional CNN sometimes utilizes transfer learning based on a training result of a training using a massive dataset (ImageNet, for example) for general image recognition. However, since the CNN in the identification device 101 is configured with the one-dimensional feature maps, the filters, the windows and the like as illustrated in FIG. 7, the number of parameters inside the CNN is small, and therefore a certain level of performance can be achieved without performing transfer learning. In other words, a number of pieces of the training image data and training time can be reduced.

Particularly, for an image identification of a malignant tumor, while distribution evaluation of local luminance and color discontinuity is important, a positional relationship between local features as considered in a two-dimensional CNN is not very important. Therefore, the CNN of the identification device 101 can extract necessary and sufficient information with a small number of parameters, compared to a standard two-dimensional CNN.

In the identifier 15 in the identification device 101, a CNN is used as the DNN, however, a DNN to which unfixed length data can be input, such as a Recurrent Neural Network (RNN), can be used instead of a CNN. In this case, the step S308 in the learning process (FIG. 8) and the re-sampling in the step S406 in the identification process (FIG. 9) will not be necessary.

When extracting a feature quantity using a DNN such as a CNN, the learning process can be performed similarly to the above-described learning process (FIG. 8), and the feature quantity extraction process can be performed similarly to the above-described identification process (FIG. 9), except for the steps S408 and S409. In the feature quantity extraction process, the values of the output layer 118 of the CNN or the values of the intermediate layer feature map of the CNN (a feature map right before the output layer, the feature map 117 in FIG. 7, is desirable) may be extracted as the feature quantity, instead of performing the step S408.

Alternatively, the value of the output layer 118 of the CNN may be used as the feature quantity vector, and the feature quantity of an image may be extracted using a distance learning method using the feature quantity vector. In this case, the feature quantity is suitable not only for identification, but also for a similarity search.

Embodiment 3

In the above-described embodiments, the parameters of the spiral curve are randomly determined in the learning process, and are set to typical values in the identification process. However, the spiral curve parameters set in the manner described above are considered to be a mixture of effective parameters and less effective parameters for identification. Therefore, in Embodiment 3, a method of searching for effective parameters as the spiral curve parameters will be described.

The spiral curve parameters are referred to as hyper parameters since they are not the parameters determined in the learning process (for example, the feature quantity extracted by the extractor 13, the weight inside the CNN, or the like). Grid search, random search, Bayesian optimization, and the like are known as methods for searching for effective hyper parameters (hyper parameter optimization method), and among these, a random search will be used in Embodiment 3.

Figure 10:
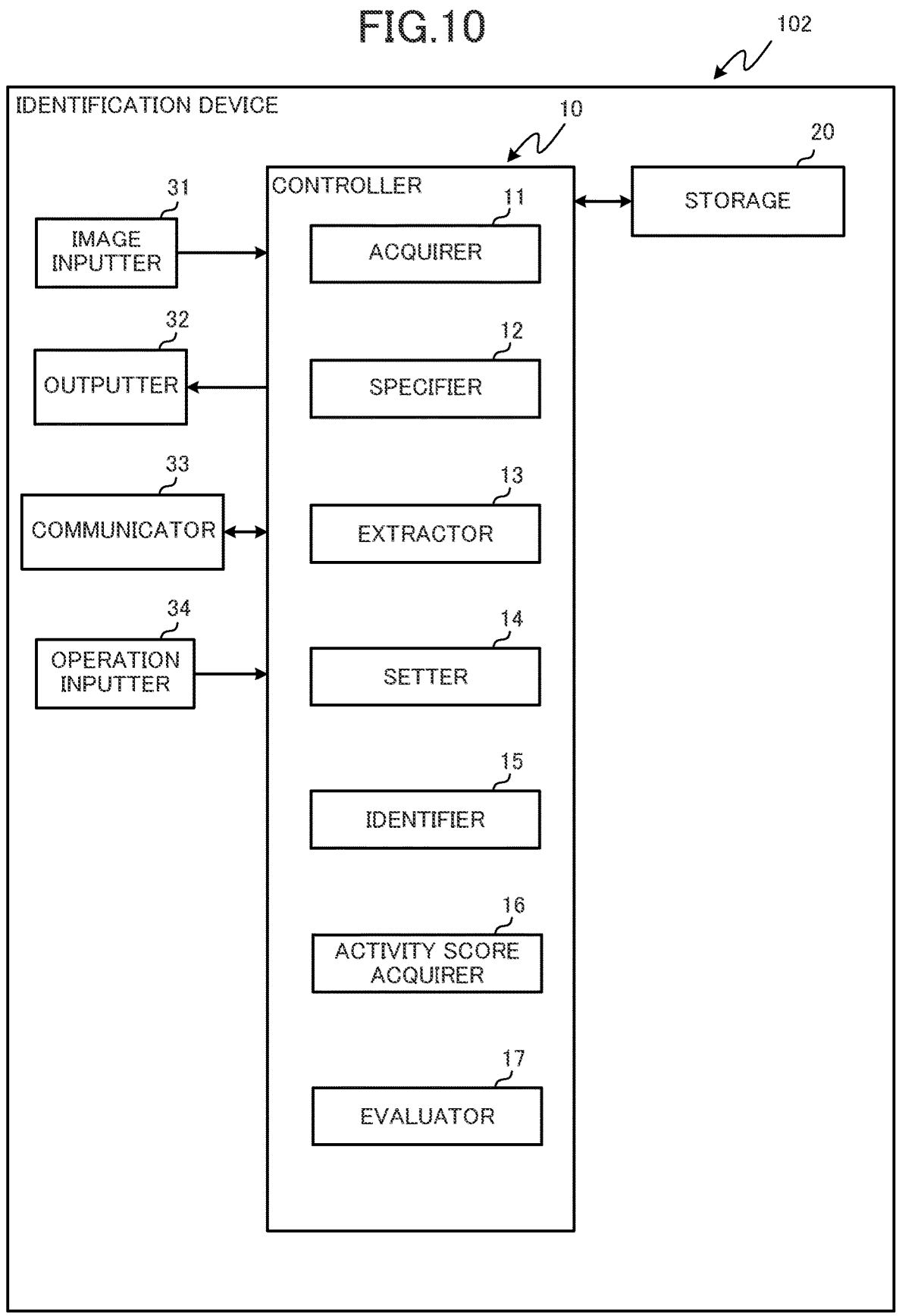
FIG. 10 is a diagram illustrating a functional configuration of an identification device according to Embodiment 3.

As illustrated in FIG. 10, an identification device 102 according to Embodiment 3 have an activity score acquirer 16 and an evaluator 17 in addition to the functional configuration of the identification device 100 according to Embodiment 1 or the identification device 101 according to Embodiment 2, as a functional configuration. An SVM or a CNN can be used as the identifier 15.

A test dataset (collection of test data) including a plurality of pieces of test data (a set of a piece of image data and a correct label for evaluation) for evaluating an identification accuracy of the identifier 15 trained in the learning process is given to the identification device 102 according to Embodiment 3. The identification device 102 searches for effective parameters for identification among a number of types of spiral curve parameters, using this test dataset. Therefore, it is desirable to provide the identification device 102 with a dataset related to an identification target as the test dataset. For example, when the identification device 102 identifies a diagnostic target on skin, sets of a piece of image data of a skin disease and a correct label are used as a test dataset.

The activity score acquirer 16 includes a two-dimensional CNN to which two-dimensional image data with vertical and horizontal directions is input, and acquires an activation map indicating influence degree that each pixel of the input image data has on the identification, using this two-dimensional CNN. Then, on the acquired activation map, based on the value (influence degree) of each pixel that can be obtained along the spiral curve, an activity score of the parameters of the spiral curve used for creating the spiral curve is acquired. The activity score of the parameters of the spiral curve is a value representing the degree of influence a pixel on the spiral curve obtained by the spiral curve parameters has on the identification, and is calculated in an activity score calculation process described later.

The evaluator 17 calculates an evaluation score being an evaluation value of the parameters of the selected spiral curve. The evaluation score is a value for evaluating the appropriateness of the parameters of the spiral curve for the identification by the identifier 15, based on an identification accuracy (and the activity score obtained by the activity score acquirer 16) of the identifier 15 learned based on the parameters of the spiral curve. Therefore, the identification accuracy of the identifier 15 is considered to increase by using parameters of a spiral curve with a high evaluation score. The evaluator 17 functions as evaluation means.

Since a learning process performed by the identification device 102 is the same as the learning processes of Embodiment 1 and Embodiment 2 (FIGS. 5 and 8), the description thereof is omitted.

Figure 9:
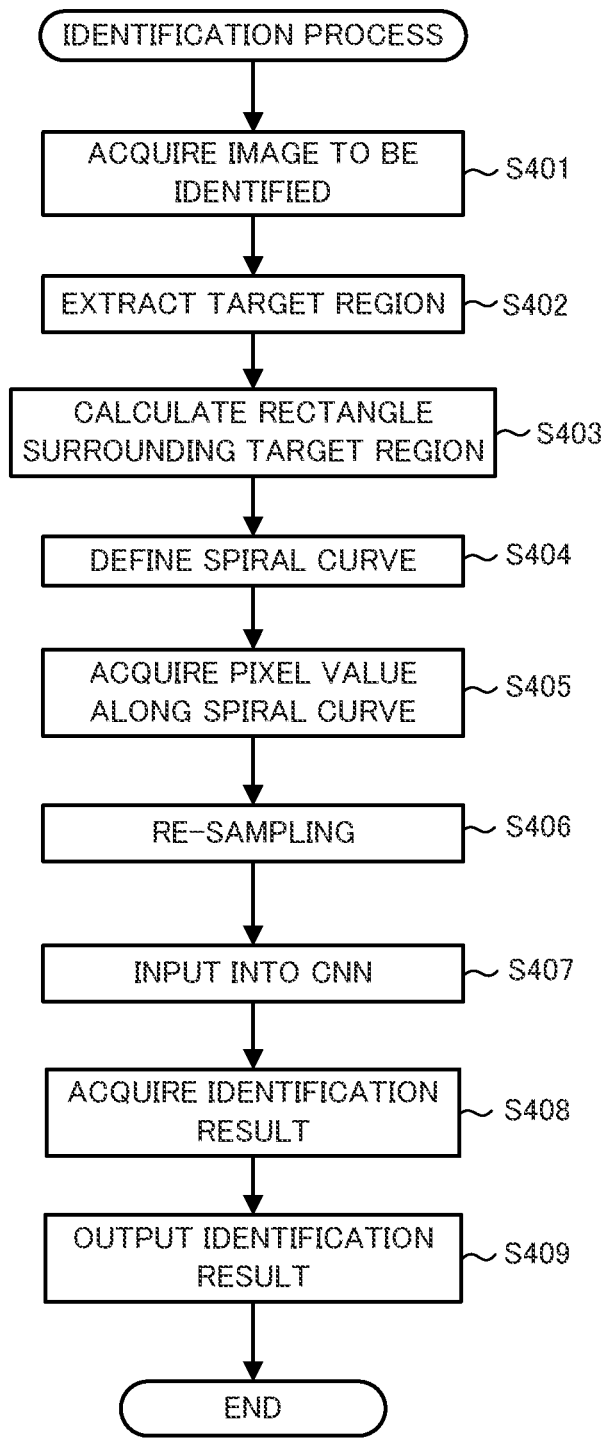
FIG. 9 is a flowchart of an identification process according to Embodiment 2.

The identification process performed by the identification device 102 is the same process as the identification processes of Embodiment 1 and Embodiment 2 (FIGS. 6 and 9), except for the process of determining the spiral curve (the step S204 in FIG. 6 and the step S404 in FIG. 9). In a process of determining a spiral curve in Embodiment 3, the specifier 12 determines a spiral curve by using spiral curve parameters selected by an optimal parameter selection process described later.

Therefore, an identification process starts when a user instructs starting of the identification process to the identification device 102 via the operation inputter 34, and the optimal parameter selection process starts right before a process of determining a spiral curve for the identification process, and when the optimal parameter selection process terminates, the process of determining the spiral curve for the identification process and thereafter are performed.

When the identification process starts, the optimal parameter selection process may be performed in parallel. Before the identification process starts, the optimal parameter selection process may be performed in advance, for example, when a user instructs the identification device 102 to start the optimal parameter selection process. By the above configuration, in the process of defining the spiral curve for the identification process, since the specifier 12 can determine the spiral curve using the spiral curve parameters selected by the optimal parameter selection process performed in advance, the optimal parameter selection process does not need to be performed in the middle of (or in parallel with) the identification process.

Figure 11:
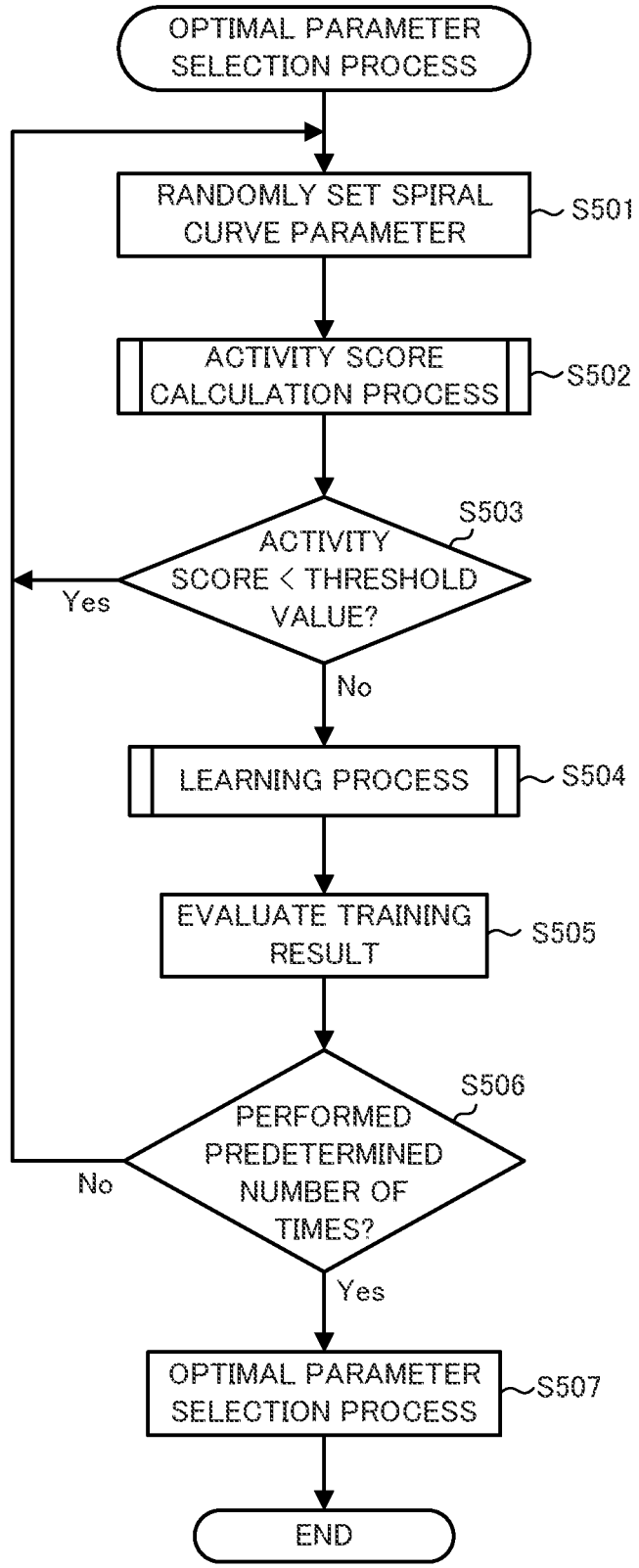
FIG. 11 is a flowchart of an optimal parameter selection process according to Embodiment 3.

Next, the optimal parameter selection process performed by the identification device 102 will be described with reference to FIG. 11. The controller 10 randomly selects spiral curve parameters (a type of the spiral curve, a number of turns, a direction, and a start angle) (step S501). This is a similar process as the spiral curve parameter setting process in the step S104 of the learning process (FIG. 5) according to Embodiment 1.

Then, the activity score acquirer 16 calculates an activity score Sm of the spiral curve parameters selected in the step S501 (step S502). The detail of the activity score calculation process will be described later.

Then, the controller 10 determines whether the activity score Sm calculated in the step S502 is less than a threshold value or not (step S503). When the activity score Sm is less than the threshold value (step S503; Yes), the process returns to the step S501.

When the activity score Sm is equal to or above the threshold value (step S503; No), the controller 10 performs a learning process (step S504). The learning process is the same as the learning process of Embodiment 1 and Embodiment 2 (FIGS. 5 and 8). In the process of randomly setting the spiral curve parameters (the step S104 in FIG. 5, the step S305 in FIG. 8), the setter 14 does not set the spiral curve parameters completely randomly but only modify slightly around the spiral curve parameters selected in the step S501.

Specifically, the type of the spiral curve is not changed among the spiral curve parameters selected in the step S501. Further, the other parameters (the number of turns of the spiral curve, the direction, and the start angle) are set within a certain range with the parameter values selected in the step S501 as the center. The parameters selected in the step S501 (parameters for optimization) are for searching optimal parameters by variously changing all of the spiral curve parameters. On the contrary, since the parameters set in the step S104 (or the step S305) in the learning process are for increasing a number of pieces of training data in accordance with the parameters selected in the step S501 in a pseudo manner, it is desirable that various parameters are set in such a way that the route of the spiral curve going through the region to be identified 42 is changed without changing the type of the spiral curve.

Then, the evaluator 17 evaluates the spiral curve parameters (parameters for evaluation) selected in the step S501 based on the identification accuracy of the identifier 15 learned in the step S504 (step S505). Specifically, the evaluator 17 acquires one-dimensional data from a linear region for evaluation being a region on a spiral curve specified using the above-described spiral curve parameters (parameters for evaluation) for each test data included in the test dataset. The evaluator 17 calculates an identification accuracy Sa as a number of correct answers/number of pieces of image data by making the identifier 15 identify the diagnostic target in the test data, based on the acquired one-dimensional data. Then, the evaluator 17 recognizes the calculated identification accuracy Sa as an evaluation score S. When a plurality of diagnostic targets exists within one piece of test image data, the evaluator 17 may identify each of the diagnostic targets, and may calculate the identification accuracy Sa as a number of correct answers/a total number of diagnostic targets in all the test data.

The evaluator 17 may calculate the evaluation score S using the following equation (1), using not only the identification accuracy Sa but also the activity score Sm calculated in the step S502. Here, $\lambda$ is an arbitrary number satisfying $0.0<\lambda<1.0$, and is set to find a weighted average using the identification accuracy Sa and the activity score Sm.

$$S=(1-\lambda)Sm+\lambda Sa \quad (1)$$

Moreover, the evaluator 17 may calculate not only the identification accuracy Sa and the activity score Sm, but also another evaluation value for evaluating the spiral curve parameters, and may find the evaluation score S using the another evaluation value instead of the identification accuracy Sa and the activity score Sm, or along with the identification accuracy Sa and the activity score Sm.

Then, the controller 10 determines whether the process from the step S501 to the step S505 has been iterated for a predetermined number of times or not (step S506). When the process has not been iterated (step S506; No), the process returns to the step S501. When the process has been repeated for the predetermined times (step S506; Yes), the controller 10 selects spiral curve parameters when the highest evaluation score S is obtained in the step S505 (highest evaluation parameters) as optimal parameters (step S507), and the process is terminated. In the step S507, the controller 10 functions as parameter selection means.

In the above-described optimal parameter selection process (FIG. 11), when the activity score calculated in the step S502 is less than a threshold value, the process immediately returns to the step S501 and re-selects spiral curve parameters. However, there may be a case where it cannot be said a low activity score certainly results in a low identification accuracy Sa. In preparation for such a case, the process of the step S503 may be skipped, and the learning process may be performed regardless of the activity score, and the training result may be evaluated.

Figure 12:
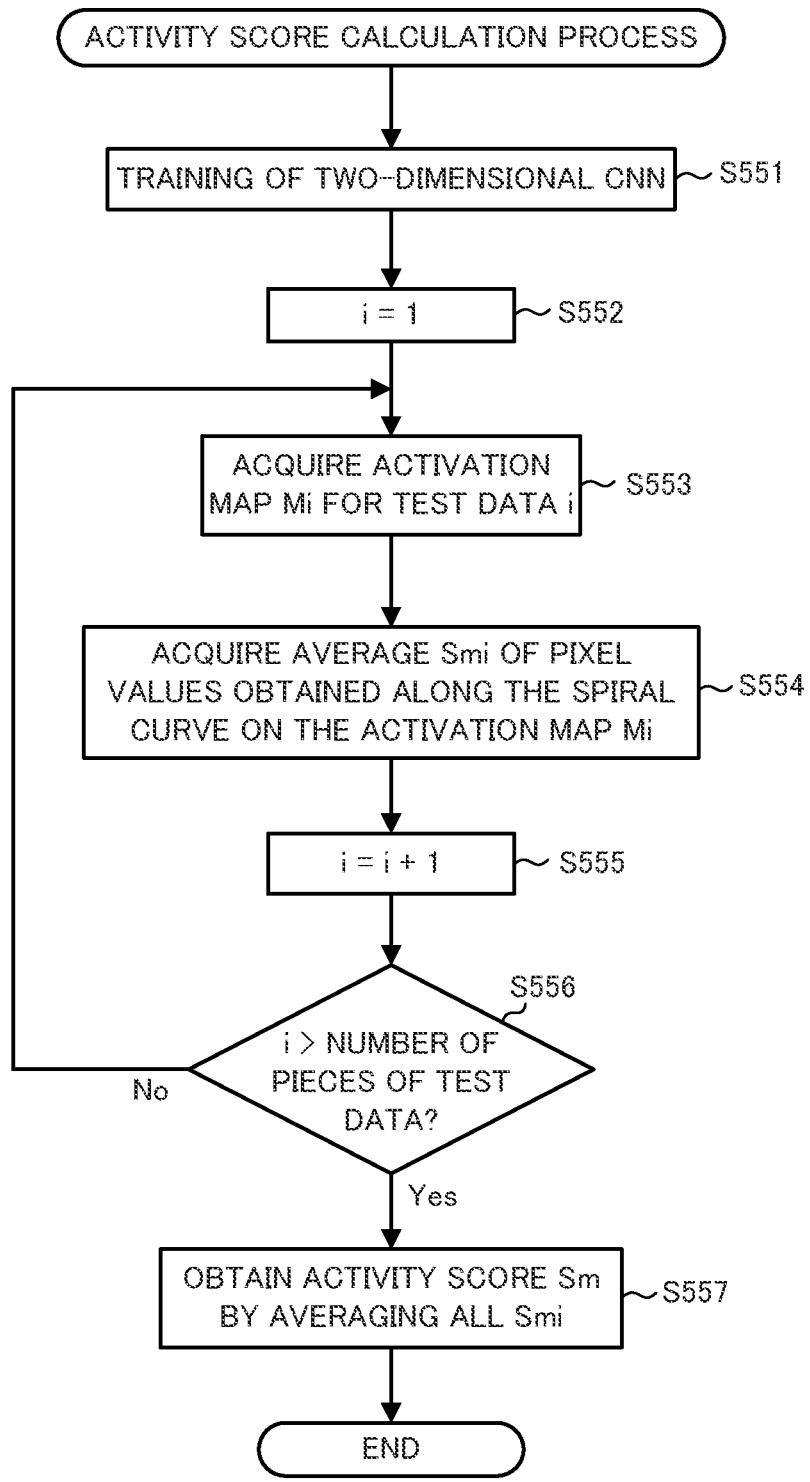
FIG. 12 is a flowchart of an activity score calculation process according to Embodiment 3.

An activity score calculation process performed in the step S502 in the optimal parameter selection process will be described with reference to FIG. 12.

The controller 10 trains a two-dimensional CNN included in the activity score acquirer 16 using training image data stored in the storage 20 (step S551). Specifically, the two-dimensional CNN is trained by iterating a process of modifying weight parameters inside the two-dimensional CNN for a predetermined number of times (for example, as many times as the number of pieces of the training image data) in such a way that a value output from the two-dimensional CNN to which a piece of training image data has been input becomes closer to a correct label assigned to the piece of training image data. Next, the controller 10 initiates a variable i for counting the pieces of test data to 1 (steps S552).

Then, the activity score acquirer 16 obtains an activation map Mi of the ith test image data (step S553). Here, a class activation mapping (CAM) is supposed to be obtained as the activation map, however, another activation map (for example, gradient-weighted class activation mapping (Grad-CAM), guided grad-CAM, or the like) may be obtained. However, in either case, each pixel value in the activation map Mi is normalized to a value between 0 and 1. In other words, when the pixel does not affect the identification at all, the value is 0, and the degree of affect is greater, the value is closer to 1.

Next, the activity score acquirer 16 draws a spiral curve using the spiral curve parameters selected in the step S501 in the optimal parameter selection process (FIG. 11) on the acquired activation map Mi, obtains pixel values along the spiral curve, and obtains Smi which is an average value of the obtained pixel values (step S554).

Then, the controller 10 increments the variable i by 1 (step S555), and determines whether the variable i is greater than the number of pieces of the test data or not (step S556). When the variable i is equal to or less than the number of pieces of the test data (step S556; No), the process returns to the step S553, and the process from steps S553 to S555 are repeated until the variable i becomes greater than the number of pieces of the test data.

When the variable i becomes greater than the number of pieces of the test data (step S556; Yes), the activity score Sm is calculated and obtained by averaging Smis for the number of pieces of the test data having obtained (step S557). The activity score calculation process is terminated, and the process of the step S503 of the optimal parameter selection process and after are performed.

In the above-described step S551, the test image data is supposed to be used as it is in the training of the two-dimensional CNN (in a standard two-dimensional CNN training process), while in the above-described step S553, the activation map is supposed to be created by obtaining one activation map (standard activation map) for one piece of test image data.

Instead of using image data of the test data as it is in the above-described manner, a rectangular region including a diagnostic target may be cut out from the image data for training the two-dimensional CNN and for creating the activation map, in a similar manner to the learning process described with reference to FIGS. 5 and 8. In this case, in the above-described step S551, the two-dimensional CNN may be trained using the size of each rectangular region cut out in the above-described manner, normalized to the size of the two-dimensional CNN. In the above-described step S554, one activation map may be obtained per each rectangle region cut out in this manner. When the percentage of the area of the diagnostic target to the entire image data is small, the calculation accuracy of the activity score is considered to increase when the rectangular region is cut out to train the two-dimensional CNN and to acquire the activation map. The activity scores may be calculated in a case where the image data is used as it is and a case where the rectangular region is cut out, respectively, and the spiral curve parameters may be evaluated based on the average value of the activity scores.

With the above-described optimal parameter selection process, in the identification process according to Embodiment 3, the identification accuracy of the identification device 102 can be increased because an identification is performed using a spiral curve defined with spiral curve parameters having the highest evaluation score (highest evaluation parameter).

By using the identification accuracy Sa of the identifier 15 for the test dataset as the evaluation score, it is possible to select spiral curve parameters that are likely to increase the identification accuracy for an identification target being similar in nature to the test data. Calculating the identification accuracy Sa takes time, however, by using the activity score Sm as the evaluation score, it is possible to select spiral curve parameters that are considered to be effective in improving the identification accuracy in a relatively short time.

In the above-described optimal parameter selection process, the random search for parameters has been used for optimizing hyperparameters, however, another method may be used. For example, when using a grid search, in the step S501, all combinations of all the parameters are selected one by one, instead of randomly selecting spiral curve parameters.

In the above-described optimal parameter selection process (FIG. 11), the evaluator 17 calculates both the activity score Sm and the identification accuracy Sa, however, both of them do not necessarily have to be calculated. In the optimal parameter selection process, the evaluator 17 may calculate one of the activity score Sm and the identification accuracy Sa, and may use the calculated value as the evaluation score S. When the activity score Sm is used as the evaluation score S, the step S504 in the optimal parameter selection process can be skipped, and in the step S505, the evaluator 17 evaluates the spiral curve parameters using the activity score Sm calculated in the step S502 as the evaluation score S.

The above-mentioned optimal parameter selection process has been described as a process for selecting optimal parameters as the spiral curve parameters during the identification process. However, the optimal parameter selection process can also be utilized when the identification process in Embodiment 2 is used as the feature extraction process. In this case, in the process of determining a spiral curve (the step S404 in FIG. 9), the specifier 12 determines a spiral curve by using the spiral curve parameters selected in the optimal parameter selection process.

Variation

In the above embodiments, a spiral curve has been adopted as "the line extending in a plurality of mutually different directions" when obtaining one-dimensional data based on pixel values. The reason is that a macroscopic feature can be captured because a spiral curve can take a long and continued linear region, and many local features can be captured (because the spiral curve contains no break points). However, "the line extending in a plurality of mutually different directions" does not have to be limited to a spiral curve.

For example, a plurality of straight lines extending from a vicinity of the center of the region to be identified, a plurality of straight lines connecting any (random) two points within the region to be identified, concentric ellipses (including concentric circles) centered in the vicinity of the center of the region to be identified, or the like may be utilized. In a case of using the above lines, the lines are plural, however, it is desirable that the data may be treated as one-dimensional data of different channels (similarly to RGB or the like) without connecting the plurality of lines, rather than connecting each of the lines and treat as one-dimensional data of one long line. This is because, unlike one spiral curve, the feature in each line can be better captured when only the continuous part is treated as one-dimensional data for one channel because the lines are not continuous.

A spiral curve, an above-described plurality of straight lines, a plurality of random straight lines, concentric ellipses and the like are robust to a rotation of an identification target because a local region on a line is directed in a plurality of directions, and a feature present in the identification target is less likely to be missed. A parallel structural feature is sometimes used in a dermoscopic diagnosis, however, the above-mentioned types of lines have an advantage of capturing such a structural feature without missing them by including a plurality of directions. A spiral curve or concentric ellipses are particularly good for extracting a feature in a circumferential direction such as an outline that matches a feature of a diseased region or the like in a dermoscopy image.

When utilizing the above-described "line extending in a plurality of mutually different directions" (not limited to a spiral curve), for example, in the step S104 in the learning process (FIG. 5), the setter 14 randomly sets parameters for defining the "line extending in a plurality of mutually different directions" (not limited to a spiral curve). Then, in the step S105, the specifier 12 defines the "line extending in a plurality of mutually different directions" extending in the region to be identified 42 from a vicinity of the center of the region to be identified 42, using the parameters set by the setter 14. Then, in the step S106, the extractor 13 obtains pixel values along the "line extending in a plurality of mutually different directions" defined by the specifier 12. These processes are similar in the steps S305 to S307 in the learning process (FIG. 8), the steps S204 to S205 in the identification process (FIG. 6), and the steps S404 to S405 in the identification process (FIG. 9).

In the optimal parameter selection process (FIG. 11), the controller 10 randomly selects spiral curve parameters in the step S501, however, this is merely an example. When using a line other than a spiral curve as the "line extending in a plurality of mutually different directions," the controller 10 may randomly select parameters defining such a line in the step S501. In this case, in the step S554 of the activity score calculation process (FIG. 12), the activity score acquirer 16 acquires pixel value along the "line extending in a plurality of mutually different directions" defined with the parameters selected in the step S501, and then acquires the value Smi being an average of the pixel values. As a result, the controller 10 becomes able to select the parameters when the highest evaluation score S is obtained as the optimal parameter in the step S507, even for parameters of a line other than a spiral curve.

In the above-described embodiment, SVM and CNN have been used as a model of the identifier 15, however, a decision tree or the like may be used instead. In Embodiment 3, CAM, Grad-CAM, Guided Grad-CAM of the CNN were exemplified as the activation map, however, the activation map utilized by the activity score acquirer 16 is not limited to these. For example, the activity score acquirer 16 may acquire an activation map of RNN, or may acquire a Saliency Map as the activation map. When the Saliency Map is acquired as the activation map, each pixel value of the activation map Mi takes a value between 0 and 1, inclusive, depending on a probability of a human eye directed at the image composed of each pixel value. In other words, the value is 0 when the human gaze is not directed to the pixel at all, and the value is closer to 1 when the pixel has a higher probability of being directed by the human gaze. When the Saliency Map is acquired as the activation map, the effect of the present disclosure will be more effectively obtained when the predetermined target in the present disclosure is an object that is easily noticed by a human eye, for example, rust of a structure, a decaying part of a vegetable, a product identified by an identification device or the like.

Variation of Image Data

In the above-described embodiments and the variation, the image data acquired by the image inputter 31 is not limited to a standard visible light image. Light irradiated to the diagnostic target may be any one of white light (light in which each wavelength in visible light is evenly mixed), light in each wavelength region including visible light near violet and ultraviolet light (invisible light) (for example, light with a wavelength of 320 nm to 440 nm, preferably 405 nm), infrared light including near infrared light (for example, light with a wavelength of 750 nm to 1000 nm, preferably 945 nm), and mixed light thereof. When receiving light (light reflected by the diagnostic target when the above-described light is irradiated, and fluorescent light generated by the irradiated light at the diagnostic target) from the diagnostic target with a light receiving device of the image inputter 31, an image data can be obtained by receiving one of the plurality of types of light (visible light, ultraviolet light, infrared light) or any mixture of these light.

For example, a skin spot can be observed by using an ultraviolet image obtained by receiving ultraviolet light from a diagnostic target part irradiated with ultraviolet light. A blood vessel can be observed by using an infrared image obtained by receiving infrared light from a diagnostic target part irradiated with infrared light. Therefore, the identification accuracy may improve by adding these images (an ultraviolet image, an infrared image and the like) to the standard visible light images.

Specifically, a spiral curve is defined in the ultraviolet image and the infrared image in a similar manner as described in the above embodiments, and one-dimensional data is obtained by acquiring pixel values (for example, values representing intensity of ultraviolet light and infrared light) along the spiral curve. Then, the obtained one-dimensional data is added in a direction of a channel (the data is treated as one-dimensional data of each separate channel, in a similar way to RGB and the like). A learning process and an identification process using the obtained one-dimensional data in multiple channels may be performed similarly to the above-described learning process (FIG. 8) and the identification process (FIG. 9) by the CNN. The ultraviolet image and the infrared image may be used on their own or in combination with another image (a visible light image, an infrared image, an ultraviolet image or the like).

Each function of the identification devices 100, 101 and 102 can be performed by a computer such as a standard personal computer (PC). Specifically, the above-described embodiments have been described supposing programs of the learning process and the searching process performed by the identification devices 100, 101, and 102 are previously stored in the ROM of the storage 20. However, the programs may be stored and distributed in a computer-readable storage medium such as a flexible disk, a compact disc read only memory (CD-ROM), a digital versatile disc (DVD), a magneto-optical disc (MO), a memory card, or a universal serial bus (USB) memory, and a computer that can realize each of the above-described functions can be configured by reading and installing the program into a computer.

The foregoing describes some example embodiments for explanatory purposes. Although the foregoing discussion has presented specific embodiments, persons skilled in the art will recognize that changes may be made in form and detail without departing from the broader spirit and scope of the invention. Accordingly, the specification and drawings are to be regarded in an illustrative rather than a restrictive sense. This detailed description, therefore, is not to be taken in a limiting sense, and the scope of the invention is defined only by the included claims, along with the full range of equivalents to which such claims are entitled.

This application claims the benefit of Japanese Patent Application No. 2019-113990, filed on Jun. 19, 2019, and Japanese Patent Application No. 2020-043778, filed on Mar. 13, 2020, of which the entirety of the disclosures is incorporated by reference herein.

INDUSTRIAL APPLICABILITY

The present disclosure can be applied to a feature quantity extracting device, a feature quantity extracting method, an identification method, an identification device, and a pro-

REFERENCE SIGNS LIST

10 Controller
11 Acquirer
12 Specifier
13 Extractor
14 Setter
15 Identifier
16 Activity score acquirer
17 Evaluator
20 Storage
31 Image inputter
32 Outputter
33 Communicator
34 Operation inputter
41 Target region
41a, 41b Regions
42 Region to be identified
43 Curve
100, 101, 102 Identification device
111 Input layer
112, 113, 114, 115, 116, 117 Feature map
118 Output layer
121, 123, 124, 125 Filter
122, 126 Windows
127 Full connection

The invention claimed is:

1. A feature quantity extracting device, comprising:
at least one processor that executes a program stored in at least one memory, wherein the at least one processor is configured to:
acquire a captured image obtained by imaging a predetermined target;
specify a linear region extending in a plurality of mutually different directions, from a region of the captured image acquired by the at least one processor, the region including the predetermined target;
obtain pixel values in the specified linear region as one-dimensional data; and
extract a feature quantity from the linear region specified by the at least one processor by calculating a predetermined statistic value for the one-dimensional data,
wherein the at least one processor is configured to obtain the pixel values in the specified linear region as one-dimensional data of each of a first component, a second component, and a third component in a predetermined color space, and extract, as the feature quantity, at least one of 16 values that are a variance of the one-dimensional data of each of the first component and the second component, a gradient and a contribution ratio of a regression line of the one-dimensional data of each of the first component, the second component, and the third component, a variance of absolute values of differences among the one-dimensional data, gradients and contribution ratios of regression lines of the first component/the second component, and the first component/the third component among ratios of the one-dimensional data, and differences of maximum values and minimum values of the one-dimensional data.

2. The feature quantity extracting device according to claim 1, wherein the linear region is a spiral-curve-shaped region.

3. The feature quantity extracting device according to claim 2, wherein the at least one process is configured to randomly set a parameter that defines a spiral curve of the spiral-curve-shaped region.

4. The feature quantity extracting device according to claim 1, wherein the predetermined target is a diagnostic target that is a target of diagnosis on human skin.

5. The feature quantity extracting device according to claim 1, wherein the at least one processor is configured to extract the feature quantity by inputting the one-dimensional data into a one-dimensional Convolutional Neural Network.

6. The feature quantity extracting device according to claim 5, wherein the at least one processor is configured to:
calculate an evaluation value that is a value representing an evaluation of appropriateness of a parameter for specifying the linear region; and
select, from a plurality of parameters, a highest evaluation parameter that is the parameter with a highest evaluation value calculated by the at least one processor, and specify the linear region using the selected highest evaluation parameter.

7. An identification device comprising:
at least one processor that executes a program stored in at least one memory, wherein the at least one processor is configured to:
acquire a captured image obtained by imaging a predetermined target;
select a parameter for evaluation from a plurality of mutually different parameters, and specify a linear region from a region including the predetermined target in image data for evaluation using the selected parameter for evaluation;
acquire one-dimensional data based on a pixel value from a linear region for evaluation that is the linear region specified by the at least one processor using the selected parameter for evaluation;
identify the predetermined target in the image data for evaluation based on the one-dimensional data acquired by the at least one processor from the linear region for evaluation;
calculate, for each of the plurality of mutually different parameters, (i) an identification accuracy of the at least one processor based on the one-dimensional data acquired from the linear region for evaluation, and (ii) an evaluation value that is a value representing an evaluation of appropriateness of a parameter for specifying a linear region, based on the identification accuracy;
select, from the plurality of mutually different parameters, a highest evaluation parameter that is the parameter with a highest evaluation value calculated by the at least one processor;
specify, using the selected highest evaluation parameter, a linear region extending in a plurality of mutually different directions, from a region of the captured image acquired by the at least one processor, the region including the predetermined target;
acquire one-dimensional data based on a pixel value, from the linear region specified by the at least one processor; and
identify the predetermined target based on the one-dimensional data acquired by the at least one processor.

8. The identification device according to claim 7, wherein the linear region is a spiral-curve-shaped region.

9. The identification device according to claim 8, wherein the at least one processor is configured to randomly set a parameter for specifying a spiral curve of the spiral-curveshaped region, and specify the spiral-curve-shaped region using a spiral curve defined by the randomly-set parameter.

10. The identification device according to claim 7, wherein the predetermined target is a diagnostic target that is a target of diagnosis on human skin.

11. The identification device according to claim 7, wherein the at least one processor is configured to identify the predetermined target in accordance with a model that has been machine-learned to use input data based on the one-dimensional data as input, and to use an identification result of the predetermined target as output.

12. The identification device according to claim 11, wherein the at least one processor is configured to:
   extract a feature quantity by calculating a predetermined statistic value for the one-dimensional data acquired by the at least one processor; and
   identify the predetermined target by inputting the feature quantity into a Support Vector Machine as the model.

13. The identification device according to claim 11, wherein the at least one processor is configured to identify the predetermined target by inputting the one-dimensional data acquired by the at least one processor into a one-dimensional Convolutional Neural Network as the model.

14. An identification device comprising:
   at least one processor that executes a program stored in at least one memory, wherein the at least one processor is configured to:
   acquire a captured image obtained by imaging a predetermined target;
   acquire, using image data for evaluation, an activation map representing an influence degree that is a degree of influence each pixel has on an identification;
   calculate an evaluation value based on the influence degree of each pixel obtained from a linear region on the activation map, the evaluation value being a value representing an evaluation of appropriateness of a parameter for specifying the linear region, and being calculated for each of a plurality of parameters;
   select, from the plurality of parameters, a highest evaluation parameter that is the parameter with a highest evaluation value calculated by the at least one processor;
   specify, using the selected highest evaluation parameter, a linear region extending in a plurality of mutually different directions, from a region of the captured image acquired by the at least one processor, the region including the predetermined target;
   acquire one-dimensional data based on a pixel value, from the linear region specified by the at least one processor; and
   identify the predetermined target based on the one-dimensional data acquired by the at least one processor.

15. A feature quantity extracting method, comprising:
   acquiring a captured image obtained by imaging a predetermined target;
   specifying a linear region extending in a plurality of mutually different directions, from a region of the acquired captured image, the region including the predetermined target;
   obtaining pixel values in the specified linear region as one-dimensional data; and
   extracting a feature quantity from the specified linear region by calculating a predetermined statistic value for the one-dimensional data,
   wherein:
   the obtaining comprises obtaining the pixel values in the specified linear region as one-dimensional data of each of a first component, a second component, and a third component in a predetermined color space, and
   the extracting comprises extracting, as the feature quantity, at least one of 16 values that are a variance of the one-dimensional data of each of the first component and the second component, a gradient and a contribution ratio of a regression line of the one-dimensional data of each of the first component, the second component, and the third component, a variance of absolute values of differences among the one-dimensional data, gradients and contribution ratios of regression lines of the first component/the second component, and the first component/the third component among ratios of the one-dimensional data, and differences of maximum values and minimum values of the one-dimensional data.

16. An identification method, comprising:
   acquiring a captured image obtained by imaging a predetermined target;
   acquiring, using image data for evaluation, an activation map representing an influence degree that is a degree of influence each pixel has on an identification;
   calculating an evaluation value based on the influence degree of each pixel obtained from a linear region on the activation map, the evaluation value being a value representing an evaluation of appropriateness of a parameter for specifying the linear region, and being calculated for each of a plurality of parameters;
   selecting, from the plurality of parameters, a highest evaluation parameter that is the parameter with a highest calculated evaluation value;
   specifying, using the selected highest evaluation parameter, a linear region extending in a plurality of mutually different directions, from a region of the acquired captured image, the region including the predetermined target;
   acquiring one-dimensional data based on a pixel value, from the specified linear region; and
   identifying the predetermined target based on the acquired one-dimensional data.

17. A non-transitory computer readable recording medium storing a program that is executable by a computer to cause the computer to perform operations comprising:
   acquiring a captured image obtained by imaging a predetermined target;
   specifying a linear region extending in a plurality of mutually different directions, from a region of the acquired captured image, the region including the predetermined target;
   obtaining pixel values in the specified linear region as one-dimensional data; and
   extracting a feature quantity from the specified linear region by calculating a predetermined statistic value for the one-dimensional data,
   wherein:
   the obtaining comprises obtaining the pixel values in the specified linear region as one-dimensional data of each of a first component, a second component, and a third component in a predetermined color space, and
   the extracting comprises extracting, as the feature quantity, at least one of 16 values that are a variance of the one-dimensional data of each of the first component and the second component, a gradient and a contribution ratio of a regression line of the one-dimensional data of each of the first component, the second component, and the third component, a variance of absolute values of differences among the one-dimensional data, gradients and contribution ratios of regression lines of the first component/the second component, and the first component/the third component among ratios of the one-dimensional data, and differences of maximum values and minimum values of the one-dimensional data.

18. A non-transitory computer readable recording medium storing a program that is executable by a computer to cause the computer to perform operations comprising:
- acquiring a captured image obtained by imaging a predetermined target;
- acquiring, using image data for evaluation, an activation map representing an influence degree that is a degree of influence each pixel has on an identification;
- calculating an evaluation value based on the influence degree of each pixel obtained from a linear region on the activation map, the evaluation value being a value representing an evaluation of appropriateness of a parameter for specifying the linear region, and being calculated for each of a plurality of parameters;
- selecting, from the plurality of parameters, a highest evaluation parameter that is the parameter with a highest calculated evaluation value;
- specifying, using the selected highest evaluation parameter, a linear region extending in a plurality of mutually different directions, from a region of the acquired captured image, the region including the predetermined target;
- acquiring one-dimensional data based on a pixel value, from the specified linear region; and
- identifying the predetermined target based on the acquired one-dimensional data.

* * * * *